US012572200B2

(12) United States Patent
Farmer et al.

(10) Patent No.: US 12,572,200 B2
(45) Date of Patent: Mar. 10, 2026

(54) AUGMENTED AND VIRTUAL REALITY DISPLAY SYSTEMS FOR OCULOMETRIC ASSESSMENTS

(71) Applicant: Magic Leap, Inc., Plantation, FL (US)

(72) Inventors: Daniel Farmer, Verdi, NV (US);
Dorion Bryce Liston, Boulder Creek, CA (US)

(73) Assignee: Magic Leap, Inc., Plantation, FL (US)

( * ) Notice: Subject to any disclaimer, the term of this patent is extended or adjusted under 35 U.S.C. 154(b) by 165 days.

(21) Appl. No.: 18/524,254

(22) Filed: Nov. 30, 2023

(65) Prior Publication Data

US 2024/0103619 A1 Mar. 28, 2024

Related U.S. Application Data

(63) Continuation of application No. 17/977,410, filed on Oct. 31, 2022, now Pat. No. 11,853,476, which is a
(Continued)

(51) Int. Cl.
*G06F 3/01* (2006.01)
*G02B 27/01* (2006.01)
*A61B 5/16* (2006.01)

(52) U.S. Cl.
CPC ......... *G06F 3/013* (2013.01); *G02B 27/0179* (2013.01); *A61B 5/163* (2017.08); *G02B 2027/0187* (2013.01)

(58) Field of Classification Search
CPC ................ G06F 3/013; G02B 27/0179; G02B 2027/0187; A61B 5/163
See application file for complete search history.

(56) References Cited

U.S. PATENT DOCUMENTS 6,850,221 B1 2/2005 Tickle
10,420,465 B1 9/2019 Stone et al.
(Continued)

FOREIGN PATENT DOCUMENTS

WO 2018/237347 A1 12/2018
WO 2020/069037 A1 4/2020

OTHER PUBLICATIONS

International Preliminary Report on Patentability received for PCT Patent Application No. PCT/US21/15558, mailed on Aug. 11, 2022, 9 pages.
(Continued)

*Primary Examiner* — Kwang-Su Yang
(74) *Attorney, Agent, or Firm* — Zi Y. Wong; Via LLP

(57) ABSTRACT

Example techniques are disclosed for increasing the sensitivity of an augmented or virtual reality display system to collecting eye-tracking data for detecting physiological conditions, such as neural processes. An example method includes accessing eye-tracking information associated with a control population and an experimental population, the eye-tracking information reflecting, for each user of the control population and the experimental population, eye-tracking metrics associated with the user; scaling the eye-tracking information based on the eye-tracking information associated with the control population; and determining a sensitivity measure reflecting a distance measure between the control population and experimental population. The sensitivity measure may be utilized to modify physical or operational parameters for the display system and/or the protocol for performing a test.

20 Claims, 17 Drawing Sheets

Related U.S. Application Data continuation of application No. 17/161,511, filed on Jan. 28, 2021, now Pat. No. 11,487,356.

(60) Provisional application No. 62/968,887, filed on Jan. 31, 2020.

(56) References Cited

U.S. PATENT DOCUMENTS

| | | | |
|---|---|---|---|
| 11,487,356 | B2 | 11/2022 | Farmer |
| 11,853,476 | B2 | 12/2023 | Farmer |
| 2006/0028436 | A1 | 2/2006 | Armstrong |
| 2007/0081123 | A1 | 4/2007 | Lewis |
| 2012/0127062 | A1 | 5/2012 | Bar-Zeev et al. |
| 2012/0162549 | A1 | 6/2012 | Gao et al. |
| 2013/0082922 | A1 | 4/2013 | Miller |
| 2013/0117377 | A1 | 5/2013 | Miller |
| 2013/0125027 | A1 | 5/2013 | Abovitz |
| 2013/0208234 | A1 | 8/2013 | Lewis |
| 2013/0242262 | A1 | 9/2013 | Lewis |
| 2014/0071539 | A1 | 3/2014 | Gao |
| 2014/0177023 | A1 | 6/2014 | Gao et al. |
| 2014/0218468 | A1 | 8/2014 | Gao et al. |
| 2014/0267420 | A1 | 9/2014 | Schowengerdt |
| 2015/0016777 | A1 | 1/2015 | Abovitz et al. |
| 2015/0103306 | A1 | 4/2015 | Kaji et al. |
| 2015/0178939 | A1 | 6/2015 | Bradski et al. |
| 2015/0205126 | A1 | 7/2015 | Schowengerdt |
| 2015/0309263 | A2 | 10/2015 | Abovitz et al. |
| 2015/0326570 | A1 | 11/2015 | Publicover et al. |
| 2015/0346495 | A1 | 12/2015 | Welch et al. |
| 2016/0011419 | A1 | 1/2016 | Gao |
| 2016/0026253 | A1 | 1/2016 | Bradski et al. |
| 2016/0262613 | A1 | 9/2016 | Klin et al. |
| 2016/0270656 | A1 | 9/2016 | Samec et al. |
| 2016/0360970 | A1 | 12/2016 | Tzvieli et al. |
| 2017/0131765 | A1 | 5/2017 | Perek et al. |
| 2017/0237974 | A1 | 8/2017 | Samec et al. |
| 2017/0290504 | A1 | 10/2017 | Khaderi et al. |
| 2017/0365101 | A1 | 12/2017 | Samec et al. |
| 2018/0121608 | A1 | 5/2018 | Gross et al. |
| 2019/0110753 | A1 | 4/2019 | Zhang et al. |
| 2019/0150727 | A1 | 5/2019 | Blaha et al. |
| 2019/0243448 | A1 | 8/2019 | Miller et al. |
| 2019/0391638 | A1 | 12/2019 | Khaderi et al. |
| 2020/0249753 | A1 | 8/2020 | Stent et al. |
| 2021/0041704 | A1 | 2/2021 | Bhargava et al. |
| 2021/0199676 | A1 * | 7/2021 | Nouso ................ G01N 33/6893 |
| 2021/0240261 | A1 | 8/2021 | Farmer |
| 2023/0067703 | A1 | 3/2023 | Farmer |

OTHER PUBLICATIONS

Office Action for Japanese Patent Application No. 2022-545997, mailed on Mar. 12, 2024, 6 pages (3 pages of English Translation and 3 pages of Original Document).

Supplementary European Search Report and Search Opinion received for European Application No. 21747281.0, mailed on Jan. 22, 2024, 8 pages.

ARToolKit: https://web.archive.org/web/20051013062315/http://www.hitl.washington.edu:80/artoolkit/documentation/hardware.htm, archived Oct. 13, 2005, 3 pages.

Azuma, "A Survey of Augmented Reality," Teleoperators and Virtual Environments 6, 4 (Aug. 1997), pp. 355-385, https://web.archive.org/web/20010604100006/http://www.cs.unc.edu/~azuma/ARpresence.pdf.

Azuma, "Predictive Tracking for Augmented Realty," TR95-007, Department of Computer Science, UNC-Chapel Hill, NC, Feb. 1995, 262 pages.

Bimber, et al., "Spatial Augmented Reality—Merging Real and Virtual Worlds," 2005, 393 pages, https://web.media.mit.edu/~raskar/book/BimberRaskarAugmentedRealityBook.pdf.

International Search Report and Written Opinion for PCT Application No. PCT/US 21 /15558, mailed Apr. 8, 2021 (MLEAP.304WO), 20 pages.

Jacob, "Eye Tracking in Advanced Interface Design," Human-Computer Interaction Lab Naval Research Laboratory, Washington, D.C. / paper/ in Virtual Environments and Advanced Interface Design, ed. by W. Barfield and T.A. Furness, pp. 258-288, Oxford University Press, New York (1995).

Liston et al., "Oculometric Assessment of Sensorimotor Impairment Associated with TBI," Optom Vis Sci., Jan. 2017, 94(1):51-59.

Tanriverdi and Jacob, "Interacting With Eye Movements in Virtual Environments," Department of Electrical Engineering and Computer Science, Tufts University, Medford, MA—paper/Proc. ACM CHI 2000 Human Factors in Computing Systems Conference, pp. 265-272, Addison-Wesley/ACM Press (2000).

* cited by examiner

1000

1002

Obtain eye-tracking information for control and experimental population

1004

Scale control and experimental population information based on control populaton information

1006

Determine sensitivity measure reflecting distance measure between experimental and control population

1100

1102

Obtain a first sensitivity measure A and a second sensitivity measure B

1104

Access display device configurations and/or oculometric protocols for the first and second sensitivity measures

1106

Perform A/B comparison

AUGMENTED AND VIRTUAL REALITY DISPLAY SYSTEMS FOR OCULOMETRIC ASSESSMENTS

CROSS-REFERENCE TO RELATED APPLICATIONS

This application is a continuation of U.S. patent application Ser. No. 17/977,410, filed Oct. 31, 2022, which is a continuation of U.S. patent application Ser. No. 17/161,511, filed Jan. 28, 2021, now U.S. Pat. No. 11,487,356, which claims the benefit of priority under 35 U.S.C. § 119 (e) to U.S. Provisional Application No. 62/968,887, filed on Jan. 31, 2020, the disclosures of which are hereby incorporated herein by reference in their entirety.

INCORPORATION BY REFERENCE

This application incorporates by reference the entireties of each of the following: U.S. Prov. Patent App. No. 62/968,887; U.S. Patent Pub. No. 2019/0243448; U.S. Patent Pub. 2016/0270656; and "Oculometric Assessment of Sensorimotor Impairment Associated with TBI", Liston D B. Wong L R, Stone L S. Optom Vis Sci. 2017 January; 94(1):51-59.

BACKGROUND

Field

The present disclosure relates to display systems and, more particularly, to augmented and virtual reality systems and devices.

Description of the Related Art

Modern computing and display technologies have facilitated the development of systems for so called "virtual reality" or "augmented reality" experiences, in which digitally reproduced images or portions thereof are presented to a user in a manner wherein they seem to be, or may be perceived as, real. A virtual reality, or "VR", scenario typically involves the presentation of digital or virtual image information without transparency to other actual real-world visual input; an augmented reality, or "AR", scenario typically involves presentation of digital or virtual image information as an augmentation to visualization of the actual world around the user. A mixed reality, or "MR", scenario is a type of AR scenario and typically involves virtual objects that are integrated into, and responsive to, the natural world. For example, an MR scenario may include AR image content that appears to be blocked by or is otherwise perceived to interact with objects in the real world.

Referring to FIG. 1, an AR scene 10 is depicted. The user of an AR technology sees a real-world park-like setting 20 featuring people, trees, buildings in the background, and a concrete platform 30. The user also perceives that he/she "sees" "virtual content" such as a robot statue 40 standing upon the real-world platform 30, and a flying cartoon-like avatar character 50 which seems to be a personification of a bumble bee. These elements 50, 40 are "virtual" in that they do not exist in the real world. In some cases, this content may be presented to a user via a head-mounted display. In some other cases, this content may be presented to a user via a portable device such as a smart phone or tablet. Because the human visual perception system and the presentation of virtual content is complex, it is challenging to produce AR technology that facilitates a comfortable, natural-feeling, rich presentation of virtual image elements amongst other virtual or real-world imagery elements.

SUMMARY

According to some embodiments, a method implemented by a system of one or more processors is described. The method comprises accessing eye-tracking information associated with a control population and an experimental population, the eye-tracking information reflecting, for each test subject of the control population and experimental population, eye-tracking metrics associated with the subject; scaling the eye-tracking information based on the eye-tracking information associated with the control population; and determining a sensitivity measure reflecting a distance measure between the control population and experimental population.

The distance measurement may advantageously be utilized to compare measurement sensitivities provided by different devices, measurement platforms, and/or measurement protocols. For example, the distance measurement may be utilized to provide a ratio between two different devices, measurement platforms, and/or measurement protocols. In some embodiments, the device, measurement platform, or measurement protocol providing the largest distance measurement between control and experiment population may be understood to provide the highest level of sensitivity for a particular condition. In some embodiments, this determination of relative sensitivity may be used to determine device or measurement protocol parameters for evaluating particular conditions. In some embodiments, the determination of relative sensitivity may be utilized to provide a selection criteria for modifying the device or measurement protocol parameters depending upon the condition to be evaluated or test to be administered.

In some embodiments, the device used to track the eye to provide measurement information may be an augmented or virtual reality display system having inwardly-facing cameras for tracking a user's eye. In such cases, the user is the test subject. Advantageously, the use of augmented or virtual reality display systems for measurement allows the ability to collect data over extended durations and, in some embodiments, allows for a plurality of tests to be administered and parameters (e.g., for the presentation of visual stimuli) to be varied and calibrated, e.g., so as to provide a high level of sensitivity for data collected from an individual user.

Some additional examples are described below.

Example 1: A method implemented by a system of one or more processors, the method comprising: accessing eye-tracking information associated with a control population and an experimental population, the eye-tracking information reflecting, for each user of the control population and experimental population, eye-tracking metrics associated with the user; scaling the eye-tracking information based on the eye-tracking information associated with the control population; and determining a sensitivity measure reflecting a distance measure between the control population and experimental population, wherein the sensitivity measure is usable to enhance identifying health conditions using eye-tracking of display devices used by users.

Example 2: The method of example 1, wherein the eye-tracking information was obtained from the display devices used by the users, the display devices having a same configuration and/or implementing a same oculometric protocol.

Example 3: The method of example 2, wherein the oculometric protocol includes the display devices having presented stimuli to the users at different perceived depths or depth planes.

Example 4: The method of example 1, wherein the experimental population includes users who have a same physiological condition and/or fall within a same cohort.

Example 5: The method of example 1, wherein scaling comprises scaling based on median and standard deviation determined from the control population.

Example 6: The method of example 1, wherein the sensitivity measure is associated with a configuration of a display device and/or an oculometric protocol.

Example 7: The method of example 1, wherein the determined sensitivity measure is compared with a different sensitive measure, the different sensitivity measure being associated with a different display device and/or a different oculometric protocol.

Example 8: A system comprising one or more processors, the system configured to present virtual content to a user of the system, wherein the system further comprises non-transitory computer storage media storing instructions that, when executed by the one or more processors, cause the one or more processors to perform operations comprising: accessing eye-tracking information associated with a control population and an experimental population, the eye-tracking information reflecting, for each user of the control population and experimental population, eye-tracking metrics associated with the user; scaling the eye-tracking information based on the eye-tracking information associated with the control population; and determining a sensitivity measure reflecting a distance measure between the control population and experimental population, wherein the sensitivity measure is usable to enhance identifying health conditions using eye-tracking of display devices used by users.

Example 9: The system of example 8, wherein the eye-tracking information was obtained from the display devices used by the users, the display devices having a same configuration and/or implementing a same oculometric protocol.

Example 10: The system of example 9, wherein the oculometric protocol includes the display devices having presented stimuli to the users at different perceived depths or depth planes.

Example 11: The system of example 8, wherein the experimental population includes users who have a same physiological condition and/or fall within a same cohort.

Example 12: The system of example 8, wherein scaling comprises scaling based on median and standard deviation determined from the control population.

Example 13: The system of example 8, wherein the sensitivity measure is associated with a configuration of a display device and/or an oculometric protocol.

Example 14: The system of example 8, wherein the determined sensitivity measure is compared with a different sensitive measure, the different sensitivity measure being associated with a different display device and/or a different oculometric protocol.

Example 15: The system of example 8, further comprising: a head-mounted display system comprising one or more processors, the head-mounted display system configured to present virtual content to a user of the head-mounted display system, wherein the head-mounted display system further comprises non-transitory computer storage media storing instructions that, when executed by the one or more processors, cause the one or more processors to access the sensitivity measure and modify an operational parameter of the head-mounted display system based on the sensitivity measure.

Example 16: The system of example 8, further comprising: a head-mounted display system comprising one or more processors, the head-mounted display system configured to present virtual content to a user of the head-mounted display system, wherein the head-mounted display system further comprises non-transitory computer storage media storing instructions that, when executed by the one or more processors, cause the one or more processors to access the sensitivity measure and modify a measurement protocol presented by the head-mounted display system based on the sensitivity measure.

Example 17: Non-transitory computer storage media storing instructions that, when executed by a system comprising one or more processors and configured to present virtual content to a user of the system, cause the one or more processors to perform operations comprising: accessing eye-tracking information associated with a control population and an experimental population, the eye-tracking information reflecting, for each user of the control population and experimental population, eye-tracking metrics associated with the user; scaling the eye-tracking information based on the eye-tracking information associated with the control population; and determining a sensitivity measure reflecting a distance measure between the control population and experimental population, wherein the sensitivity measure is usable to enhance identifying health conditions using eye-tracking of display devices used by users.

Example 18: The computer storage media of example 17, wherein the eye-tracking information was obtained from the display devices used by the users, the display devices having a same configuration and/or implementing a same oculometric protocol.

Example 19: The computer storage media of example 18, wherein the oculometric protocol includes the display devices having presented stimuli to the users at different perceived depths or depth planes.

Example 20: The computer storage media of example 17, wherein the sensitivity measure is associated with a configuration of a display device and/or an oculometric protocol.

DETAILED DESCRIPTION

Figure 1:
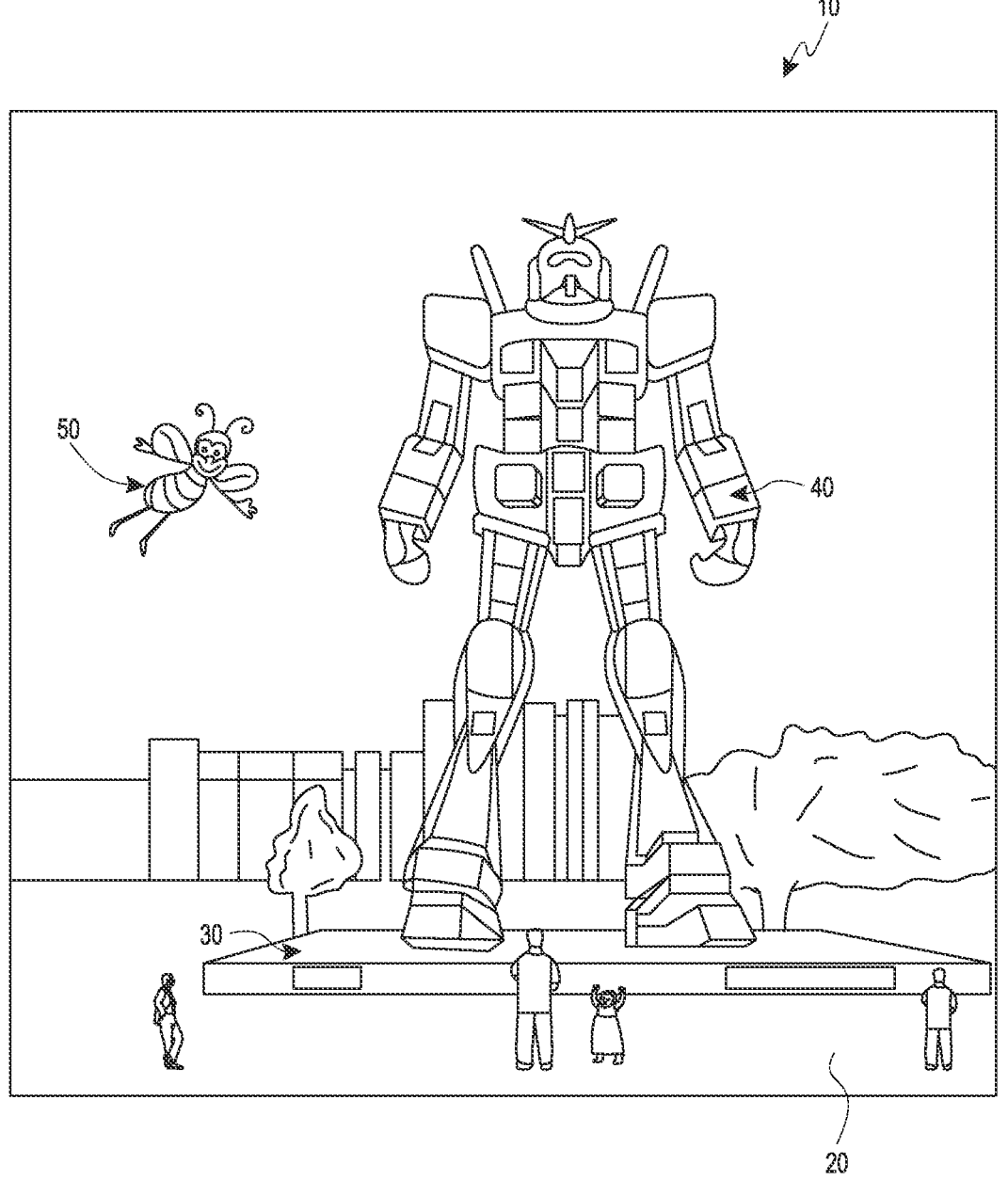
FIG. 1 illustrates a user's view of augmented reality (AR) through an AR device.

Described herein are techniques to analyze eye-movement information to improve the sensitivity of a device or measurement protocol for obtaining data used to quantify physiological conditions, such as neural processes, of a test subject or a population of test subjects. In some embodiments, the measurement device may be a display device, and test subjects may be users of the display device. The display devices may include sensors, such as image sensors (e.g. cameras), used to perform eye-tracking. In addition to being utilized to test for physiological conditions, the eye-tracking, as an example, may be used to inform presentation of virtual reality, augmented reality, or mixed reality, content (referred to herein as "virtual content"). An example display device is described below, with respect to FIGS. 2-9E.

It will be appreciated that certain health information for a person may be determined based on tracking the person's eye-movements in response to stimuli (e.g., visual stimuli). For example, oculomotor behavior may reflect functional consequences of neural pathology. As an example, signs of psychiatric illness may be determined based on tracking horizontal eye movements of a person as the person views a swinging pendulum. As additional examples, certain qualitative oculomotor signs of drug toxicity, brain injury, neurological diseases and so on, may, be determined based on a subject's eye-movement. However, eye-tracking devices which have historically been used have been specialized hardware. For example, a person may be required to travel to his/her health professional to undergo eye-tracking based tests, which may limit the availability of such tests.

In contrast, the display devices described herein may be advantageously configured to perform eye-tracking while users utilize the display devices in a normal course of operation. For example, a user may use a display device to view virtual content (e.g., the robot statue 40) described above. In this example, the virtual content may be entertaining to the user. As described herein, the virtual content may be presented such that it is perceived to be fixed in the real-world. To effectuate this presentation, the display device may leverage sensors, such as eye-tracking image sensors, to obtain images or video of the user's eyes. Based on these images and information indicating a head pose of the user, virtual content may be updated and perceived.

Based on the eye-tracking, a user may be determined to have certain oculomotor behavior which is indicative of the user having a certain physiological condition or of the user falling within a cohort of persons. An example cohort may include people who share one or more conditions, such as people with a same physiological condition, people who worked a same job (e.g., a professional sports league, a construction job), people who lived in a same geographic area, and so on.

It will be appreciated that different devices, different operational parameters on a particular device, different measurement protocols, etc. may provide different levels of sensitivity to data relevant for detecting a particular condition. Consequently, the ability to compare sensitivities across different devices, different operational parameters, different measurement protocols, etc., may be beneficial for selection of appropriate devices, operational parameters, measurement protocols, etc., for collecting eye-tracking measurements for detecting particular conditions. In some embodiments, the comparisons disclosed herein may advantageously allow operational parameters and measurement protocols (e.g., tests presented) to be selected to allow for increased sensitivity for a particular user or cohort.

For example, the display devices described herein may be associated with different configurations, with each configuration being more, or less, sensitive to measuring data for detection of a physiological condition or a cohort. Example configurations may vary based on particular image sensors used, image sensor positions, techniques to illuminate an eye, exposure and/or sampling rate used, mechanical decoupling, algorithmic selections, and so on. For example, a first display device may be capable of determining a gaze of a user at a first frequency (e.g., 30 Hz). Additionally, this first display device may determine gaze according to a first technique. In contrast, a second display device may be capable of determining a gaze of the user at a second frequency (e.g., 90 Hz). This second display device may determine gaze according to a second technique which may be distinct from that of the first technique. Thus, the first display device and the second display device may have a different configuration (that is, may be the same device with two different configurations or two different devices). As will be described, these display devices may have different sensitivities to detecting certain physiological conditions or whether users fall within certain cohorts.

As described herein, a sensitivity measure (e.g., a scalar value) may be determined for a particular configuration of a display device. The sensitivity measure may represent a sensitivity of the display device with respect to determining a distance measure between a control population and an experimental population. For example, the experimental population may include persons who share a particular physiological condition and/or fall within a particular cohort. Thus, and as an example, the sensitivity measure may indicate how sensitive a particular configuration is for the detection of the particular physiological condition. In addition or alternatively, the sensitivity measure may be determined for a particular oculometric protocol. An example oculometric protocol may include particular virtual content which is to be presented to a user. For example, a first oculometric protocol may present certain visual patterns at certain times. As another example, a second oculometric protocol may present different visual patterns. In some embodiments, oculometric protocols may present virtual content at different depths and/or different perceived three-dimensional positions from a user.

These sensitivity measures may be used to perform "A/B" comparisons between a first configuration of a display device and a second configuration of a display device. In this way, it may be determined that certain features of the first configuration enable greater sensitivity with respect to determining a difference between a control population and an experimental population.

Additionally, a display device may use these sensitivity measures to provide health information for a user. For example, it may be determined that certain configurations and/or certain oculometric protocols are advantageous (e.g., optimal) for determining the presence of respective physiological conditions. Thus, a first configuration and/or a first oculometric protocol may be advantageous for a first physiological condition. Thus, the display device may optionally assume different configurations as a user uses the display device. For example, the display device may adjust one or more of, image sensor positions, illumination techniques, exposure information, sampling rates, algorithmic selections, and so on. The display device may also select different oculometric protocols. Thus, the display device may present different virtual content to a user. For each adjustment of a configuration and/or adjustment of an oculometric protocol, the display device may determine a likelihood of the user having an associated physiological condition. With respect to the first configuration described above, the display device may determine a likelihood of the user having the first physiological condition.

In this way, the techniques described herein may be usable to detect whether certain protocols are more sensitive to certain conditions (e.g., physiological conditions) and/or certain conditions in certain populations. For example, A/B testing may be performed to test whether one protocol is more sensitive than another for signs of a particular condition than another (e.g., optionally keeping the population and device fixed). As another example, A/B testing may be performed to test for differences between two devices (e.g., optionally keeping the protocol and population fixed). Thus, the techniques may be usable to enhance eye tracking techniques to identify health conditions in certain populations using devices.

Example Augmented Reality Display Systems

Figure 2:
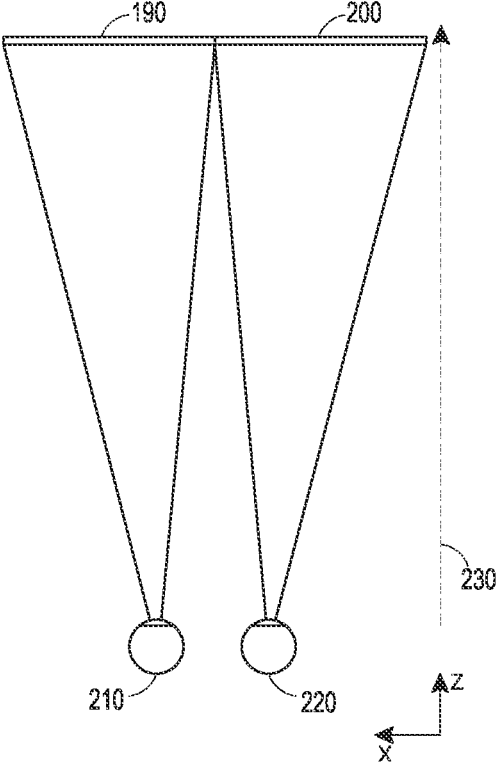
FIG. 2 illustrates a conventional display system for simulating three-dimensional imagery for a user.

FIG. 2 illustrates a conventional display system for simulating three-dimensional imagery for a user. It will be appreciated that a user's eyes are spaced apart and that, when looking at a real object in space, each eye will have a slightly different view of the object and may form an image of the object at different locations on the retina of each eye. This may be referred to as binocular disparity and may be utilized by the human visual system to provide a perception of depth. Conventional display systems simulate binocular disparity by presenting two distinct images 190, 200 with slightly different views of the same virtual object—one for each eye 210, 220—corresponding to the views of the virtual object that would be seen by each eye were the virtual object a real object at a desired depth. These images provide binocular cues that the user's visual system may interpret to derive a perception of depth.

With continued reference to FIG. 2, the images 190, 200 are spaced from the eyes 210, 220 by a distance 230 on a z-axis. The z-axis is parallel to the optical axis of the viewer with their eyes fixated on an object at optical infinity directly ahead of the viewer. The images 190, 200 are flat and at a fixed distance from the eyes 210, 220. Based on the slightly different views of a virtual object in the images presented to the eyes 210, 220, respectively, the eyes may naturally rotate such that an image of the object falls on corresponding points on the retinas of each of the eyes, to maintain single binocular vision. This rotation may cause the lines of sight of each of the eyes 210, 220 to converge onto a point in space at which the virtual object is perceived to be present. As a result, providing three-dimensional imagery conventionally involves providing binocular cues that may manipulate the vergence of the user's eyes 210, 220, and that the human visual system interprets to provide a perception of depth.

Figure 3A:
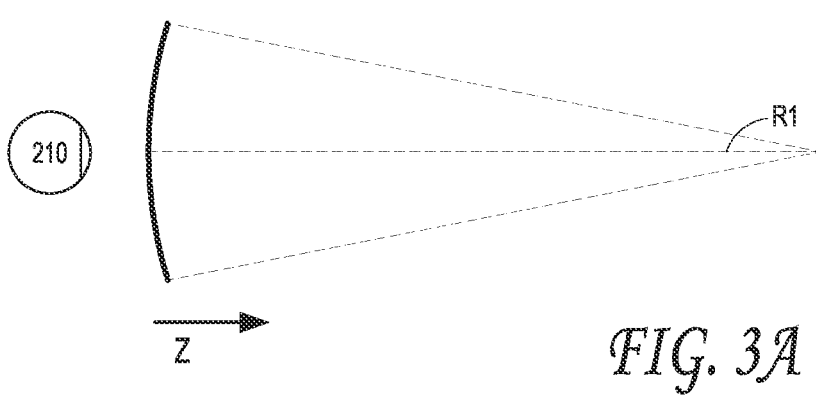
FIGS. 3A-3C illustrate relationships between radius of curvature and focal radius.
Figure 3B:
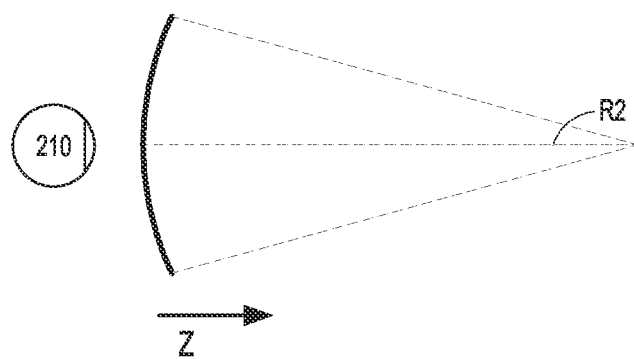
Figure 3C:
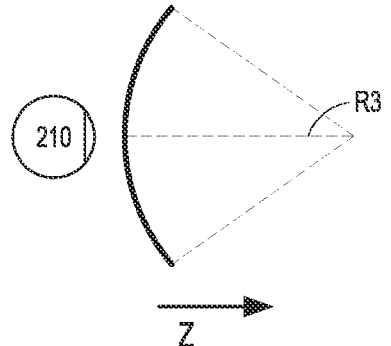

Generating a realistic and comfortable perception of depth is challenging, however. It will be appreciated that light from objects at different distances from the eyes have wavefronts with different amounts of divergence. FIGS. 3A-3C illustrate relationships between distance and the divergence of light rays. The distance between the object and the eye 210 is represented by, in order of decreasing distance, R1, R2, and R3. As shown in FIGS. 3A-3C, the light rays become more divergent as distance to the object decreases. Conversely, as distance increases, the light rays become more collimated. Stated another way, it may be said that the light field produced by a point (the object or a part of the object) has a spherical wavefront curvature, which is a function of how far away the point is from the eye of the user. The curvature increases with decreasing distance between the object and the eye 210. While only a single eye 210 is illustrated for clarity of illustration in FIGS. 3A-3C and other figures herein, the discussions regarding eye 210 may be applied to both eyes 210 and 220 of a viewer.

With continued reference to FIGS. 3A-3C, light from an object that the viewer's eyes are fixated on may have different degrees of wavefront divergence. Due to the different amounts of wavefront divergence, the light may be focused differently by the lens of the eye, which in turn may require the lens to assume different shapes to form a focused image on the retina of the eye. Where a focused image is not formed on the retina, the resulting retinal blur acts as a cue to accommodation that causes a change in the shape of the lens of the eye until a focused image is formed on the retina. For example, the cue to accommodation may trigger the ciliary muscles surrounding the lens of the eye to relax or contract, thereby modulating the force applied to the suspensory ligaments holding the lens, thus causing the shape of the lens of the eye to change until retinal blur of an object of fixation is eliminated or minimized, thereby forming a focused image of the object of fixation on the retina (e.g., fovea) of the eye. The process by which the lens of the eye changes shape may be referred to as accommodation, and the shape of the lens of the eye required to form a focused image of the object of fixation on the retina (e.g., fovea) of the eye may be referred to as an accommodative state.

Figure 4A:
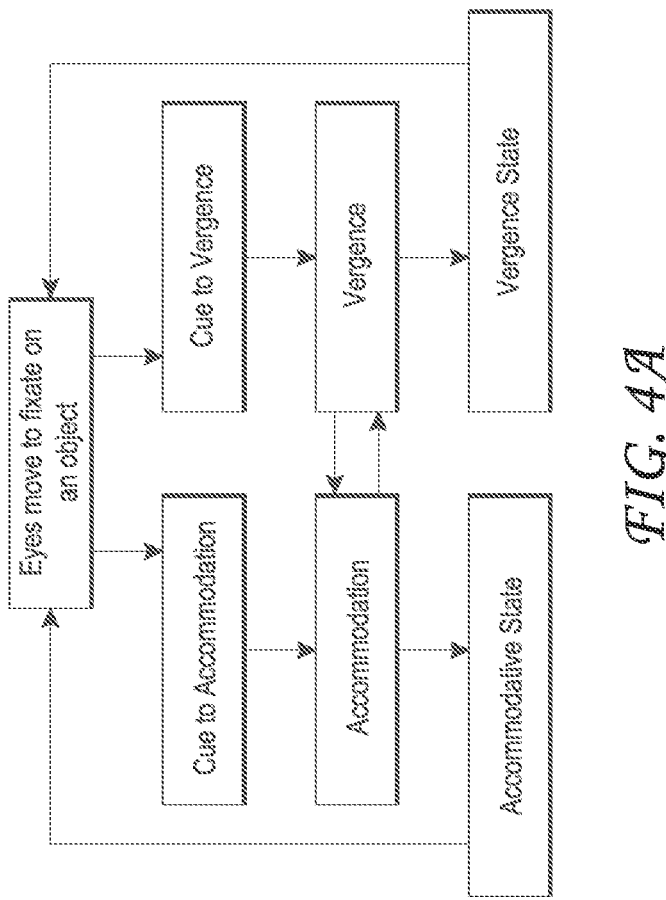
FIG. 4A illustrates a representation of the accommodation-vergence response of the human visual system.

With reference now to FIG. 4A, a representation of the accommodation-vergence response of the human visual system is illustrated. The movement of the eyes to fixate on an object causes the eyes to receive light from the object, with the light forming an image on each of the retinas of the eyes. The presence of retinal blur in the image formed on the retina may provide a cue to accommodation, and the relative locations of the image on the retinas may provide a cue to vergence. The cue to accommodation causes accommodation to occur, resulting in the lenses of the eyes each assuming a particular accommodative state that forms a focused image of the object on the retina (e.g., fovea) of the eye. On the other hand, the cue to vergence causes vergence movements (rotation of the eyes) to occur such that the images formed on each retina of each eye are at corresponding retinal points that maintain single binocular vision. In these positions, the eyes may be said to have assumed a particular vergence state. With continued reference to FIG.

4A, accommodation may be understood to be the process by which the eye achieves a particular accommodative state, and vergence may be understood to be the process by which the eye achieves a particular vergence state. As indicated in FIG. 4A, the accommodative and vergence states of the eyes may change if the user fixates on another object. For example, the accommodated state may change if the user fixates on a new object at a different depth on the z-axis.

Without being limited by theory, it is believed that viewers of an object may perceive the object as being "three-dimensional" due to a combination of vergence and accommodation. As noted above, vergence movements (e.g., rotation of the eyes so that the pupils move toward or away from each other to converge the lines of sight of the eyes to fixate upon an object) of the two eyes relative to each other are closely associated with accommodation of the lenses of the eyes. Under normal conditions, changing the shapes of the lenses of the eyes to change focus from one object to another object at a different distance will automatically cause a matching change in vergence to the same distance, under a relationship known as the "accommodation-vergence reflex." Likewise, a change in vergence will trigger a matching change in lens shape under normal conditions.

Figure 4B:
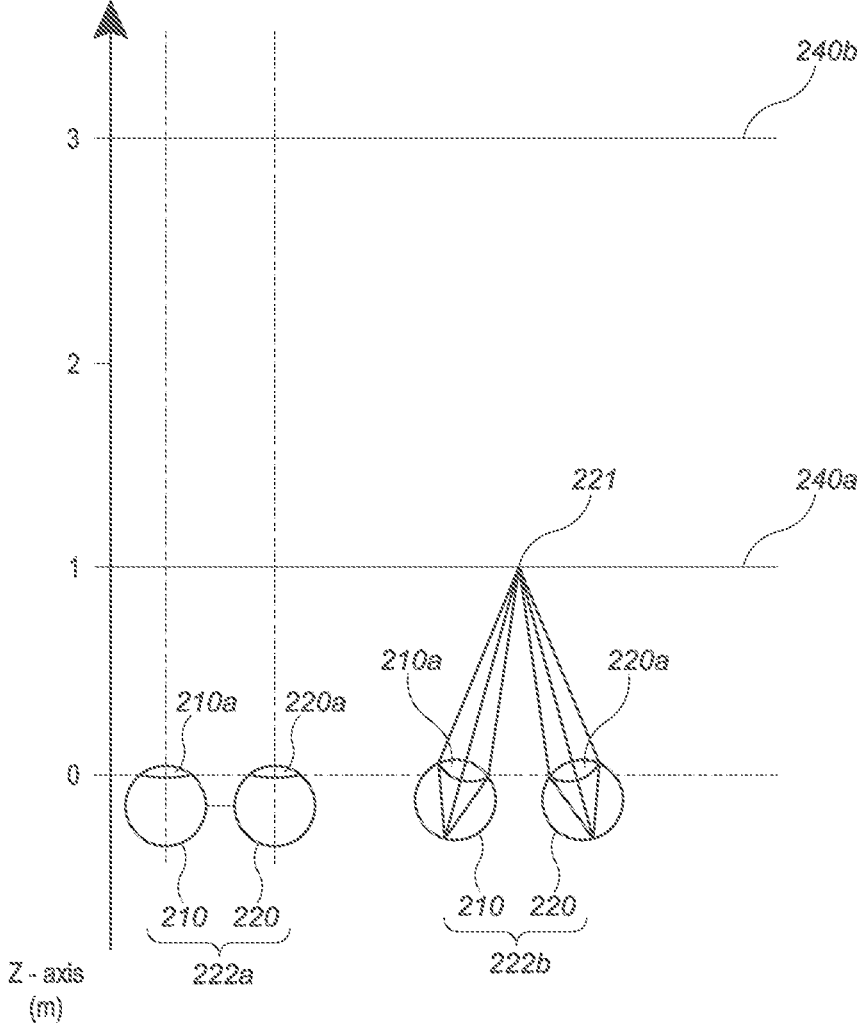
FIG. 4B illustrates examples of different accommodative states and vergence states of a pair of eyes of the user.

With reference now to FIG. 4B, examples of different accommodative and vergence states of the eyes are illustrated. The pair of eyes 222a is fixated on an object at optical infinity, while the pair eyes 222b are fixated on an object 221 at less than optical infinity. Notably, the vergence states of each pair of eyes is different, with the pair of eyes 222a directed straight ahead, while the pair of eyes 222 converge on the object 221. The accommodative states of the eyes forming each pair of eyes 222a and 222b are also different, as represented by the different shapes of the lenses 210a, 220a.

Undesirably, many users of conventional "3-D" display systems find such conventional systems to be uncomfortable or may not perceive a sense of depth at all due to a mismatch between accommodative and vergence states in these displays. As noted above, many stereoscopic or "3-D" display systems display a scene by providing slightly different images to each eye. Such systems are uncomfortable for many viewers, since they, among other things, simply provide different presentations of a scene and cause changes in the vergence states of the eyes, but without a corresponding change in the accommodative states of those eyes. Rather, the images are shown by a display at a fixed distance from the eyes, such that the eyes view all the image information at a single accommodative state. Such an arrangement works against the "accommodation-vergence reflex" by causing changes in the vergence state without a matching change in the accommodative state. This mismatch is believed to cause viewer discomfort. Display systems that provide a better match between accommodation and vergence may form more realistic and comfortable simulations of three-dimensional imagery.

Without being limited by theory, it is believed that the human eye typically may interpret a finite number of depth planes to provide depth perception. Consequently, a highly believable simulation of perceived depth may be achieved by providing, to the eye, different presentations of an image corresponding to each of these limited numbers of depth planes. In some embodiments, the different presentations may provide both cues to vergence and matching cues to accommodation, thereby providing physiologically correct accommodation-vergence matching.

With continued reference to FIG. 4B, two depth planes 240, corresponding to different distances in space from the eyes 210, 220, are illustrated. For a given depth plane 240, vergence cues may be provided by the displaying of images of appropriately different perspectives for each eye 210, 220. In addition, for a given depth plane 240, light forming the images provided to each eye 210, 220 may have a wavefront divergence corresponding to a light field produced by a point at the distance of that depth plane 240.

In the illustrated embodiment, the distance, along the z-axis, of the depth plane 240 containing the point 221 is 1 m. As used herein, distances or depths along the z-axis may be measured with a zero-point located at the exit pupils of the user's eyes. Thus, a depth plane 240 located at a depth of 1 m corresponds to a distance of 1 m away from the exit pupils of the user's eyes, on the optical axis of those eyes with the eyes directed towards optical infinity. As an approximation, the depth or distance along the z-axis may be measured from the display in front of the user's eyes (e.g., from the surface of a waveguide), plus a value for the distance between the device and the exit pupils of the user's eyes. That value may be called the eye relief and corresponds to the distance between the exit pupil of the user's eye and the display worn by the user in front of the eye. In practice, the value for the eye relief may be a normalized value used generally for all viewers. For example, the eye relief may be assumed to be 20 mm and a depth plane that is at a depth of 1 m may be at a distance of 980 mm in front of the display.

Figures 4C, 4D:
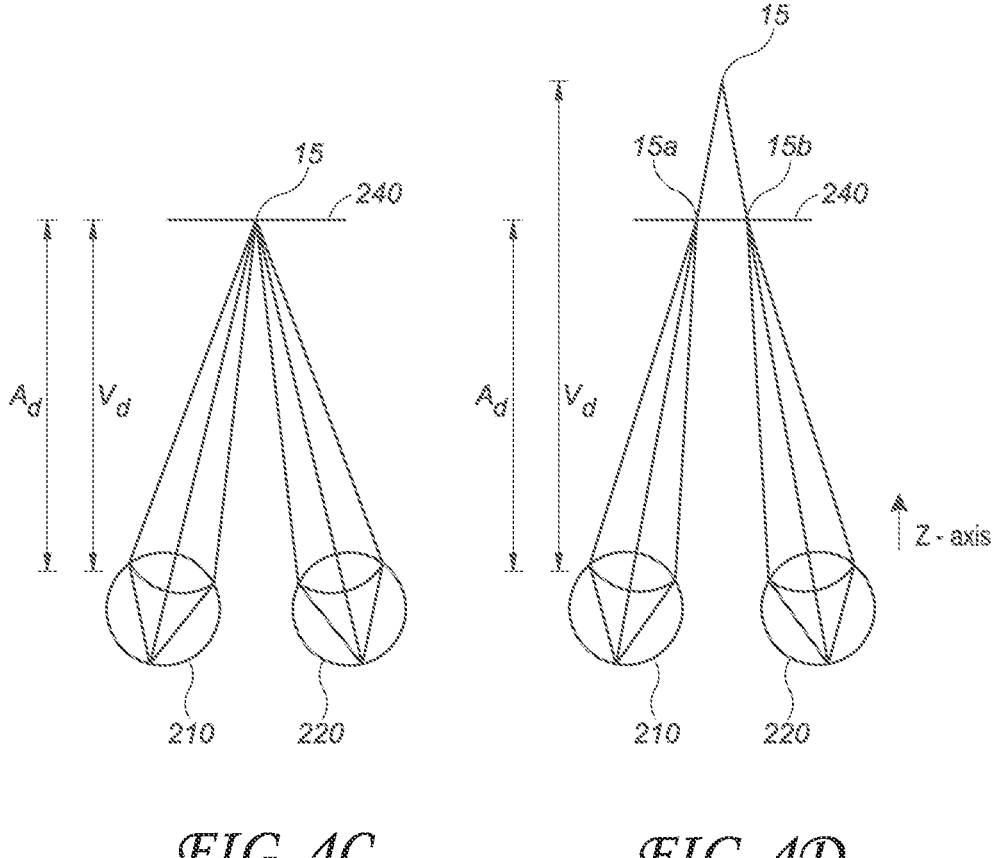
FIG. 4C illustrates an example of a representation of a top-down view of a user viewing content via a display system.
FIG. 4D illustrates another example of a representation of a top-down view of a user viewing content via a display system.

With reference now to FIGS. 4C and 4D, examples of matched accommodation-vergence distances and mismatched accommodation-vergence distances are illustrated, respectively. As illustrated in FIG. 4C, the display system may provide images of a virtual object to each eye 210, 220. The images may cause the eyes 210, 220 to assume a vergence state in which the eyes converge on a point 15 on a depth plane 240. In addition, the images may be formed by a light having a wavefront curvature corresponding to real objects at that depth plane 240. As a result, the eyes 210, 220 assume an accommodative state in which the images are in focus on the retinas of those eyes. Thus, the user may perceive the virtual object as being at the point 15 on the depth plane 240.

It will be appreciated that each of the accommodative and vergence states of the eyes 210, 220 are associated with a particular distance on the z-axis. For example, an object at a particular distance from the eyes 210, 220 causes those eyes to assume particular accommodative states based upon the distances of the object. The distance associated with a particular accommodative state may be referred to as the accommodation distance, $A_d$. Similarly, there are particular vergence distances, $V_d$, associated with the eyes in particular vergence states, or positions relative to one another. Where the accommodation distance and the vergence distance match, the relationship between accommodation and vergence may be said to be physiologically correct. This is considered to be the most comfortable scenario for a viewer.

In stereoscopic displays, however, the accommodation distance and the vergence distance may not always match. For example, as illustrated in FIG. 4D, images displayed to the eyes 210, 220 may be displayed with wavefront divergence corresponding to depth plane 240, and the eyes 210, 220 may assume a particular accommodative state in which the points 15a, 15b on that depth plane are in focus. However, the images displayed to the eyes 210, 220 may provide cues for vergence that cause the eyes 210, 220 to converge on a point 15 that is not located on the depth plane 240. As a result, the accommodation distance corresponds to the distance from the exit pupils of the eyes 210, 220 to the depth plane 240, while the vergence distance corresponds to the larger distance from the exit pupils of the eyes 210, 220 to the point 15, in some embodiments. The accommodation distance is different from the vergence distance. Consequently, there is an accommodation-vergence mismatch. Such a mismatch is considered undesirable and may cause discomfort in the user. It will be appreciated that the mismatch corresponds to distance (e.g., $V_d$–$A_d$) and may be characterized using diopters.

In some embodiments, it will be appreciated that a reference point other than exit pupils of the eyes 210, 220 may be utilized for determining distance for determining accommodation-vergence mismatch, so long as the same reference point is utilized for the accommodation distance and the vergence distance. For example, the distances could be measured from the cornea to the depth plane, from the retina to the depth plane, from the eyepiece (e.g., a waveguide of the display device) to the depth plane, and so on.

Without being limited by theory, it is believed that users may still perceive accommodation-vergence mismatches of up to about 0.25 diopter, up to about 0.33 diopter, and up to about 0.5 diopter as being physiologically correct, without the mismatch itself causing significant discomfort. In some embodiments, display systems disclosed herein (e.g., the display system 250, FIG. 6) present images to the viewer having accommodation-vergence mismatch of about 0.5 diopter or less. In some other embodiments, the accommodation-vergence mismatch of the images provided by the display system is about 0.33 diopter or less. In yet other embodiments, the accommodation-vergence mismatch of the images provided by the display system is about 0.25 diopter or less, including about 0.1 diopter or less.

Figure 5:
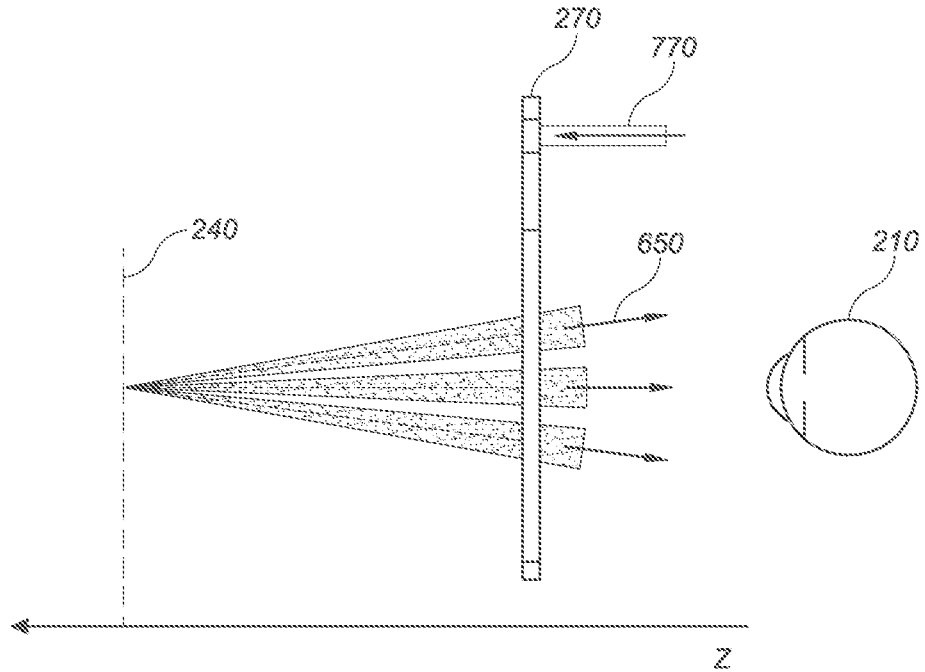
FIG. 5 illustrates aspects of an approach for simulating three-dimensional imagery by modifying wavefront divergence.

FIG. 5 illustrates aspects of an approach for simulating three-dimensional imagery by modifying wavefront divergence. The display system includes a waveguide 270 that is configured to receive light 770 that is encoded with image information, and to output that light to the user's eye 210. The waveguide 270 may output the light 650 with a defined amount of wavefront divergence corresponding to the wavefront divergence of a light field produced by a point on a desired depth plane 240. In some embodiments, the same amount of wavefront divergence is provided for all objects presented on that depth plane. In addition, it will be illustrated that the other eye of the user may be provided with image information from a similar waveguide.

In some embodiments, a single waveguide may be configured to output light with a set amount of wavefront divergence corresponding to a single or limited number of depth planes and/or the waveguide may be configured to output light of a limited range of wavelengths. Consequently, in some embodiments, a plurality or stack of waveguides may be utilized to provide different amounts of wavefront divergence for different depth planes and/or to output light of different ranges of wavelengths. As used herein, it will be appreciated at a depth plane may be planar or may follow the contours of a curved surface.

Figure 6:
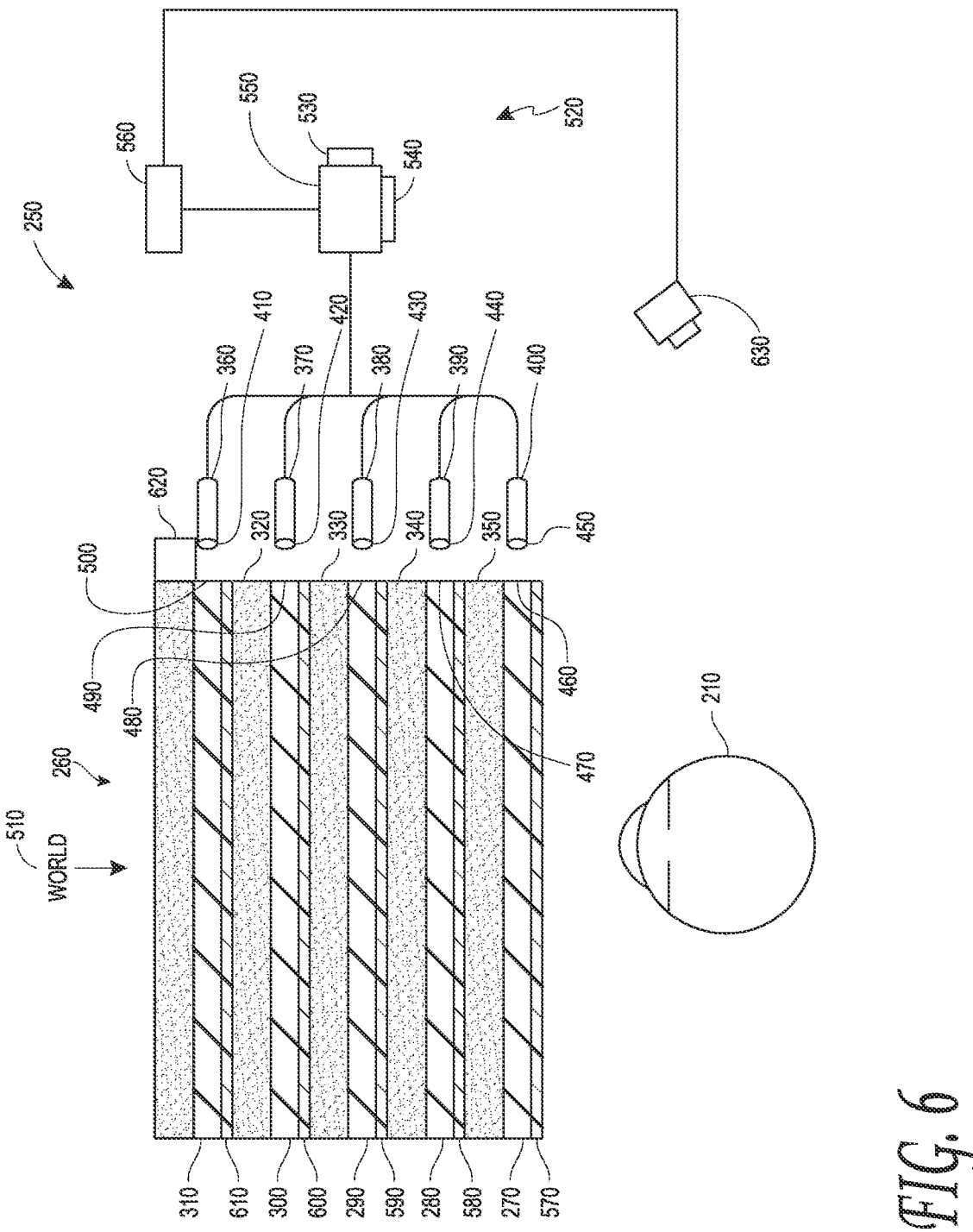
FIG. 6 illustrates an example of a waveguide stack for outputting image information to a user.

FIG. 6 illustrates an example of a waveguide stack for outputting image information to a user. A display system 250 includes a stack of waveguides, or stacked waveguide assembly, 260 that may be utilized to provide three-dimensional perception to the eye/brain using a plurality of waveguides 270, 280, 290, 300, 310. It will be appreciated that the display system 250 may be considered a light field display in some embodiments. In addition, the waveguide assembly 260 may also be referred to as an eyepiece.

In some embodiments, the display system 250 may be configured to provide substantially continuous cues to vergence and multiple discrete cues to accommodation. The cues to vergence may be provided by displaying different images to each of the eyes of the user, and the cues to accommodation may be provided by outputting the light that forms the images with selectable discrete amounts of wavefront divergence. Stated another way, the display system 250 may be configured to output light with variable levels of wavefront divergence. In some embodiments, each discrete level of wavefront divergence corresponds to a particular depth plane and may be provided by a particular one of the waveguides 270, 280, 290, 300, 310.

With continued reference to FIG. 6, the waveguide assembly 260 may also include a plurality of features 320, 330, 340, 350 between the waveguides. In some embodiments, the features 320, 330, 340, 350 may be one or more lenses. The waveguides 270, 280, 290, 300, 310 and/or the plurality of lenses 320, 330, 340, 350 may be configured to send image information to the eye with various levels of wavefront curvature or light ray divergence. Each waveguide level may be associated with a particular depth plane and may be configured to output image information corresponding to that depth plane. Image injection devices 360, 370, 380, 390, 400 may function as a source of light for the waveguides and may be utilized to inject image information into the waveguides 270, 280, 290, 300, 310, each of which may be configured, as described herein, to distribute incoming light across each respective waveguide, for output toward the eye 210. Light exits an output surface 410, 420, 430, 440, 450 of the image injection devices 360, 370, 380, 390, 400 and is injected into a corresponding input surface 460, 470, 480, 490, 500 of the waveguides 270, 280, 290, 300, 310. In some embodiments, each of the input surfaces 460, 470, 480, 490, 500 may be an edge of a corresponding waveguide, or may be part of a major surface of the corresponding waveguide (that is, one of the waveguide surfaces directly facing the world 510 or the viewer's eye 210). In some embodiments, a single beam of light (e.g. a collimated beam) may be injected into each waveguide to output an entire field of cloned collimated beams that are directed toward the eye 210 at particular angles (and amounts of divergence) corresponding to the depth plane associated with a particular waveguide. In some embodiments, a single one of the image injection devices 360, 370, 380, 390, 400 may be associated with and inject light into a plurality (e.g., three) of the waveguides 270, 280, 290, 300, 310.

In some embodiments, the image injection devices 360, 370, 380, 390, 400 are discrete displays that each produce image information for injection into a corresponding waveguide 270, 280, 290, 300, 310, respectively. In some other embodiments, the image injection devices 360, 370, 380, 390, 400 are the output ends of a single multiplexed display which may, e.g., pipe image information via one or more optical conduits (such as fiber optic cables) to each of the image injection devices 360, 370, 380, 390, 400. It will be appreciated that the image information provided by the image injection devices 360, 370, 380, 390, 400 may include light of different wavelengths, or colors (e.g., different component colors, as discussed herein).

In some embodiments, the light injected into the waveguides 270, 280, 290, 300, 310 is provided by a light projection system 520, which comprises a light module 530, which may include a light emitter, such as a light emitting diode (LED). The light from the light module 530 may be directed to and modified by a light modulator 540, e.g., a spatial light modulator, via a beam splitter 550. The light modulator 540 may be configured to change the perceived intensity of the light injected into the waveguides 270, 280, 290, 300, 310 to encode the light with image information. Examples of spatial light modulators include liquid crystal displays (LCD) including a liquid crystal on silicon (LCOS) displays. In some other embodiments, the spatial light modulator may be a MEMS device, such as a digital light processing (DLP) device. It will be appreciated that the image injection devices 360, 370, 380, 390, 400 are illustrated schematically and, in some embodiments, these image injection devices may represent different light paths and locations in a common projection system configured to output light into associated ones of the waveguides 270, 280, 290, 300, 310. In some embodiments, the waveguides of the waveguide assembly 260 may function as ideal lens while relaying light injected into the waveguides out to the user's eyes. In this conception, the object may be the spatial light modulator 540 and the image may be the image on the depth plane.

In some embodiments, the display system 250 may be a scanning fiber display comprising one or more scanning fibers configured to project light in various patterns (e.g., raster scan, spiral scan, Lissajous patterns, etc.) into one or more waveguides 270, 280, 290, 300, 310 and ultimately to the eye 210 of the viewer. In some embodiments, the illustrated image injection devices 360, 370, 380, 390, 400 may schematically represent a single scanning fiber or a bundle of scanning fibers configured to inject light into one or a plurality of the waveguides 270, 280, 290, 300, 310. In some other embodiments, the illustrated image injection devices 360, 370, 380, 390, 400 may schematically represent a plurality of scanning fibers or a plurality of bundles of scanning fibers, each of which are configured to inject light into an associated one of the waveguides 270, 280, 290, 300, 310. It will be appreciated that one or more optical fibers may be configured to transmit light from the light module 530 to the one or more waveguides 270, 280, 290, 300, 310. It will be appreciated that one or more intervening optical structures may be provided between the scanning fiber, or fibers, and the one or more waveguides 270, 280, 290, 300, 310 to, e.g., redirect light exiting the scanning fiber into the one or more waveguides 270, 280, 290, 300, 310.

A controller 560 controls the operation of one or more of the stacked waveguide assembly 260, including operation of the image injection devices 360, 370, 380, 390, 400, the light source 530, and the light modulator 540. In some embodiments, the controller 560 is part of the local data processing module 140. The controller 560 includes programming (e.g., instructions in a non-transitory medium) that regulates the timing and provision of image information to the waveguides 270, 280, 290, 300, 310 according to, e.g., any of the various schemes disclosed herein. In some embodiments, the controller may be a single integral device, or a distributed system connected by wired or wireless communication channels. The controller 560 may be part of the processing modules 140 or 150 (FIG. 9E) in some embodiments.

With continued reference to FIG. 6, the waveguides 270, 280, 290, 300, 310 may be configured to propagate light within each respective waveguide by total internal reflection (TIR). The waveguides 270, 280, 290, 300, 310 may each be planar or have another shape (e.g., curved), with major top and bottom surfaces and edges extending between those major top and bottom surfaces. In the illustrated configuration, the waveguides 270, 280, 290, 300, 310 may each include out-coupling optical elements 570, 580, 590, 600, 610 that are configured to extract light out of a waveguide by redirecting the light, propagating within each respective waveguide, out of the waveguide to output image information to the eye 210. Extracted light may also be referred to as out-coupled light and the out-coupling optical elements light may also be referred to light extracting optical elements. An extracted beam of light may be outputted by the waveguide at locations at which the light propagating in the waveguide strikes a light extracting optical element. The out-coupling optical elements 570, 580, 590, 600, 610 may, for example, be gratings, including diffractive optical features, as discussed further herein. While illustrated disposed at the bottom major surfaces of the waveguides 270, 280, 290, 300, 310, for ease of description and drawing clarity, in some embodiments, the out-coupling optical elements 570, 580, 590, 600, 610 may be disposed at the top and/or bottom major surfaces, and/or may be disposed directly in the volume of the waveguides 270, 280, 290, 300, 310, as discussed further herein. In some embodiments, the out-coupling optical elements 570, 580, 590, 600, 610 may be formed in a layer of material that is attached to a transparent substrate to form the waveguides 270, 280, 290, 300, 310. In some other embodiments, the waveguides 270, 280, 290, 300, 310 may be a monolithic piece of material and the out-coupling optical elements 570, 580, 590, 600, 610 may be formed on a surface and/or in the interior of that piece of material.

With continued reference to FIG. 6, as discussed herein, each waveguide 270, 280, 290, 300, 310 is configured to output light to form an image corresponding to a particular depth plane. For example, the waveguide 270 nearest the eye may be configured to deliver collimated light (which was injected into such waveguide 270), to the eye 210. The collimated light may be representative of the optical infinity focal plane. The next waveguide up 280 may be configured to send out collimated light which passes through the first lens 350 (e.g., a negative lens) before it may reach the eye 210; such first lens 350 may be configured to create a slight convex wavefront curvature so that the eye/brain interprets light coming from that next waveguide up 280 as coming from a first focal plane closer inward toward the eye 210 from optical infinity. Similarly, the third up waveguide 290 passes its output light through both the first 350 and second 340 lenses before reaching the eye 210; the combined optical power of the first 350 and second 340 lenses may be configured to create another incremental amount of wavefront curvature so that the eye/brain interprets light coming from the third waveguide 290 as coming from a second focal plane that is even closer inward toward the person from optical infinity than was light from the next waveguide up 280.

The other waveguide layers 300, 310 and lenses 330, 320 are similarly configured, with the highest waveguide 310 in the stack sending its output through all of the lenses between it and the eye for an aggregate focal power representative of the closest focal plane to the person. To compensate for the stack of lenses 320, 330, 340, 350 when viewing/interpreting light coming from the world 510 on the other side of the stacked waveguide assembly 260, a compensating lens layer 620 may be disposed at the top of the stack to compensate for the aggregate power of the lens stack 320, 330, 340, 350 below. Such a configuration provides as many perceived focal planes as there are available waveguide/lens pairings. Both the out-coupling optical elements of the waveguides and the focusing aspects of the lenses may be static (i.e., not dynamic or electro-active). In some alternative embodiments, either or both may be dynamic using electro-active features.

In some embodiments, two or more of the waveguides 270, 280, 290, 300, 310 may have the same associated depth plane. For example, multiple waveguides 270, 280, 290, 300, 310 may be configured to output images set to the same depth plane, or multiple subsets of the waveguides 270, 280, 290, 300, 310 may be configured to output images set to the same plurality of depth planes, with one set for each depth plane. This may provide advantages for forming a tiled image to provide an expanded field of view at those depth planes.

With continued reference to FIG. 6, the out-coupling optical elements 570, 580, 590, 600, 610 may be configured to both redirect light out of their respective waveguides and to output this light with the appropriate amount of divergence or collimation for a particular depth plane associated with the waveguide. As a result, waveguides having different associated depth planes may have different configurations of out-coupling optical elements 570, 580, 590, 600, 610, which output light with a different amount of divergence depending on the associated depth plane. In some embodiments, the light extracting optical elements 570, 580, 590, 600, 610 may be volumetric or surface features, which may be configured to output light at specific angles. For example, the light extracting optical elements 570, 580, 590, 600, 610 may be volume holograms, surface holograms, and/or diffraction gratings. In some embodiments, the features 320, 330, 340, 350 may not be lenses; rather, they may simply be spacers (e.g., cladding layers and/or structures for forming air gaps).

In some embodiments, the out-coupling optical elements 570, 580, 590, 600, 610 are diffractive features that form a diffraction pattern, or "diffractive optical element" (also referred to herein as a "DOE"). Preferably, the DOE's have a sufficiently low diffraction efficiency so that only a portion of the light of the beam is deflected away toward the eye 210 with each intersection of the DOE, while the rest continues to move through a waveguide via TIR. The light carrying the image information is thus divided into a number of related exit beams that exit the waveguide at a multiplicity of locations and the result is a fairly uniform pattern of exit emission toward the eye 210 for this particular collimated beam bouncing around within a waveguide.

In some embodiments, one or more DOEs may be switchable between "on" states in which they actively diffract, and "off" states in which they do not significantly diffract. For instance, a switchable DOE may comprise a layer of polymer dispersed liquid crystal, in which microdroplets comprise a diffraction pattern in a host medium, and the refractive index of the microdroplets may be switched to substantially match the refractive index of the host material (in which case the pattern does not appreciably diffract incident light) or the microdroplet may be switched to an index that does not match that of the host medium (in which case the pattern actively diffracts incident light).

In some embodiments, a camera assembly 630 (e.g., a digital camera, including visible light and infrared light cameras) may be provided to capture images of the eye 210 and/or tissue around the eye 210 to, e.g., detect user inputs and/or to monitor the physiological state of the user. As used herein, a camera may be any image capture device. In some embodiments, the camera assembly 630 may include an image capture device and a light source to project light (e.g., infrared light) to the eye, which may then be reflected by the eye and detected by the image capture device. In some embodiments, the camera assembly 630 may be attached to the frame or support structure 80 (FIG. 9E) and may be in electrical communication with the processing modules 140 and/or 150, which may process image information from the camera assembly 630. In some embodiments, one camera assembly 630 may be utilized for each eye, to separately monitor each eye.

The camera assembly 630 may, in some embodiments, observe movements of the user, such as the user's eye movements. As an example, the camera assembly 630 may capture images of the eye 210 to determine the size, position, and/or orientation of the pupil of the eye 210 (or some other structure of the eye 210). The camera assembly 630 may, if desired, obtain images (processed by processing circuitry of the type described herein) used to determine the direction the user is looking (e.g., eye pose or gaze direction). In some embodiments, camera assembly 630 may include multiple cameras, at least one of which may be utilized for each eye, to separately determine the eye pose or gaze direction of each eye independently. The camera assembly 630 may, in some embodiments and in combination with processing circuitry such as the controller 560 or the local data processing module 140, determine eye pose or gaze direction based on glints (e.g., reflections) of reflected light (e.g., infrared light) from a light source included in camera assembly 630.

Figure 7:
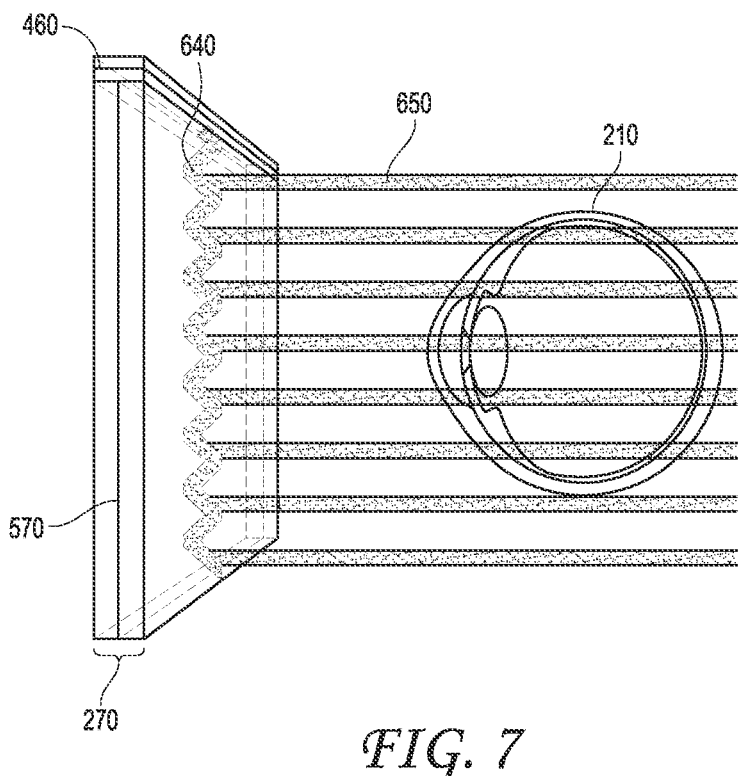
FIG. 7 illustrates an example of exit beams outputted by a waveguide.

With reference now to FIG. 7, an example of exit beams outputted by a waveguide is shown. One waveguide is illustrated, but it will be appreciated that other waveguides in the waveguide assembly 260 (FIG. 6) may function similarly, where the waveguide assembly 260 includes multiple waveguides. Light 640 is injected into the waveguide 270 at the input surface 460 of the waveguide 270 and propagates within the waveguide 270 by TIR. At points where the light 640 impinges on the DOE 570, a portion of the light exits the waveguide as exit beams 650. The exit beams 650 are illustrated as substantially parallel but, as discussed herein, they may also be redirected to propagate to the eye 210 at an angle (e.g., forming divergent exit beams), depending on the depth plane associated with the waveguide 270. It will be appreciated that substantially parallel exit beams may be indicative of a waveguide with out-coupling optical elements that out-couple light to form images that appear to be set on a depth plane at a large distance (e.g., optical infinity) from the eye 210. Other waveguides or other sets of out-coupling optical elements may output an exit beam pattern that is more divergent, which would require the eye 210 to accommodate to a closer distance to bring it into focus on the retina and would be interpreted by the brain as light from a distance closer to the eye 210 than optical infinity.

Figure 8:
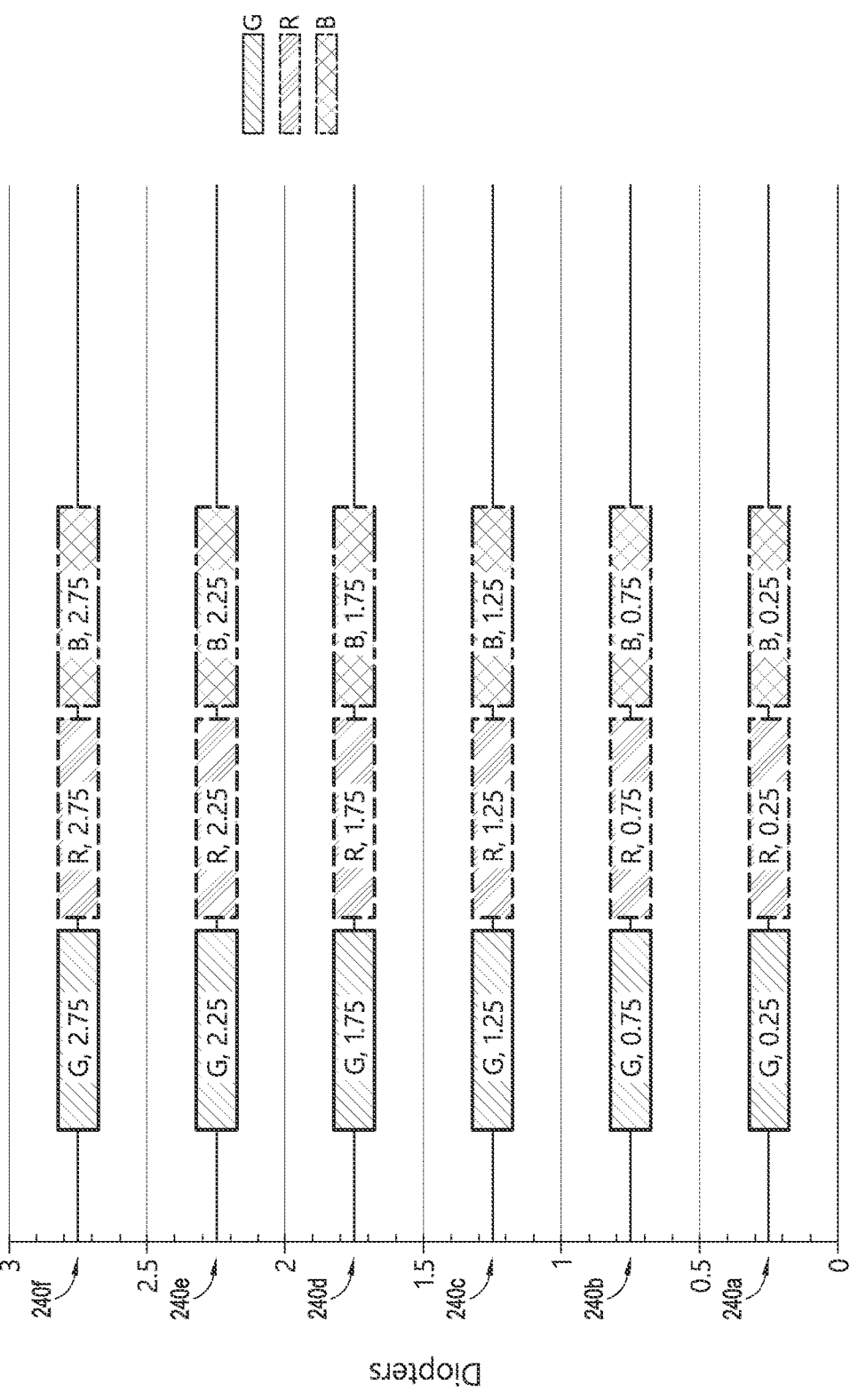
FIG. 8 illustrates an example of a stacked eyepiece in which each depth plane includes images formed using multiple different component colors.

In some embodiments, a full color image may be formed at each depth plane by overlaying images in each of the component colors, e.g., three or more component colors. FIG. 8 illustrates an example of a stacked waveguide assembly in which each depth plane includes images formed using multiple different component colors. The illustrated embodiment shows depth planes 240a-240f, although more or fewer depths are also contemplated. Each depth plane may have three or more component color images associated with it, including: a first image of a first color, G; a second image of a second color, R; and a third image of a third color, B. Different depth planes are indicated in the figure by different numbers for diopters (dpt) following the letters G, R, and B. Just as examples, the numbers following each of these letters indicate diopters (1/m), or inverse distance of the depth plane from a viewer, and each box in the figures represents an individual component color image. In some embodiments, to account for differences in the eye's focusing of light of different wavelengths, the exact placement of the depth planes for different component colors may vary. For example, different component color images for a given depth plane may be placed on depth planes corresponding to different distances from the user. Such an arrangement may increase visual acuity and user comfort and/or may decrease chromatic aberrations.

In some embodiments, light of each component color may be outputted by a single dedicated waveguide and, consequently, each depth plane may have multiple waveguides associated with it. In such embodiments, each box in the figures including the letters G, R, or B may be understood to represent an individual waveguide, and three waveguides may be provided per depth plane where three component color images are provided per depth plane. While the waveguides associated with each depth plane are shown adjacent to one another in this drawing for ease of description, it will be appreciated that, in a physical device, the waveguides may all be arranged in a stack with one waveguide per level. In some other embodiments, multiple component colors may be outputted by the same waveguide, such that, e.g., only a single waveguide may be provided per depth plane.

With continued reference to FIG. 8, in some embodiments, G is the color green, R is the color red, and B is the color blue. In some other embodiments, other colors associated with other wavelengths of light, including magenta and cyan, may be used in addition to or may replace one or more of red, green, or blue.

It will be appreciated that references to a given color of light throughout this disclosure will be understood to encompass light of one or more wavelengths within a range of wavelengths of light that are perceived by a viewer as being of that given color. For example, red light may include light of one or more wavelengths in the range of about 620-780 nm, green light may include light of one or more wavelengths in the range of about 492-577 nm, and blue light may include light of one or more wavelengths in the range of about 435-493 nm.

In some embodiments, the light source 530 (FIG. 6) may be configured to emit light of one or more wavelengths outside the visual perception range of the viewer, for example, infrared and/or ultraviolet wavelengths. In addition, the in-coupling, out-coupling, and other light redirecting structures of the waveguides of the display 250 may be configured to direct and emit this light out of the display towards the user's eye 210, e.g., for imaging and/or user stimulation applications.

Figure 9A:
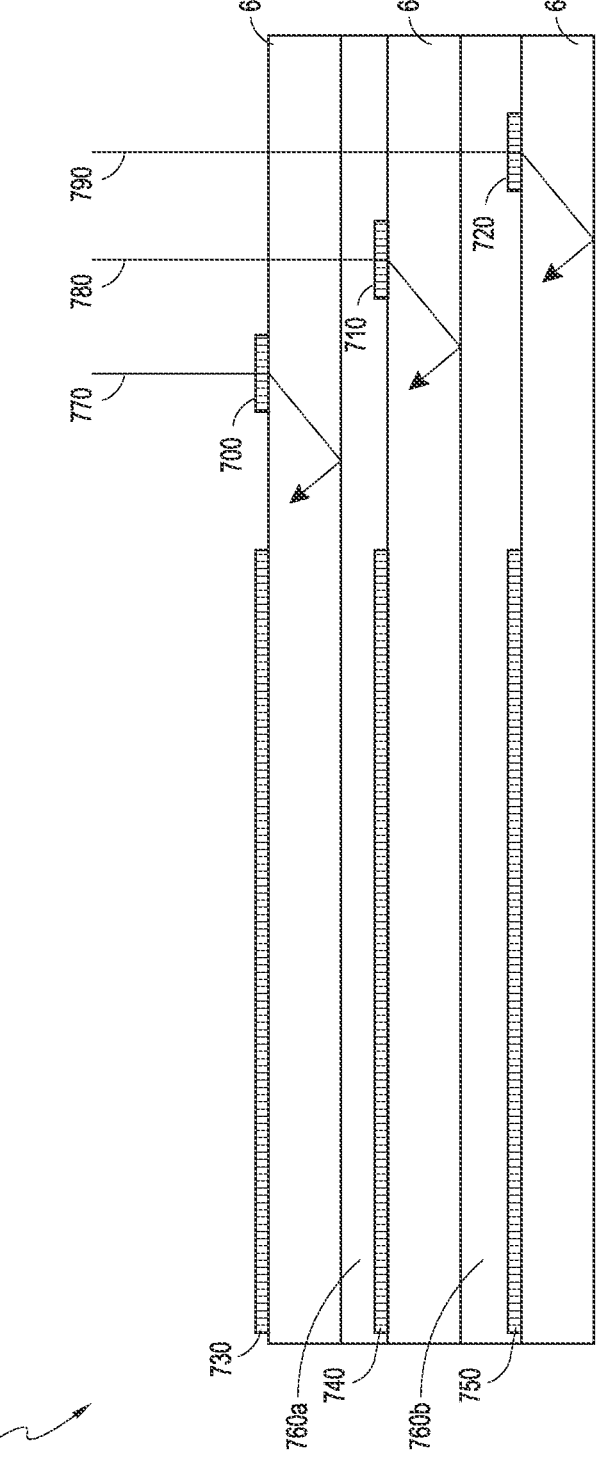
FIG. 9A illustrates a cross-sectional side view of an example of a set of stacked waveguides that each includes an in-coupling optical element.

With reference now to FIG. 9A, in some embodiments, light impinging on a waveguide may need to be redirected to in-couple that light into the waveguide. An in-coupling optical element may be used to redirect and in-couple the light into its corresponding waveguide. FIG. 9A illustrates a cross-sectional side view of an example of a plurality or set 660 of stacked waveguides that each includes an in-coupling optical element. The waveguides may each be configured to output light of one or more different wavelengths, or one or more different ranges of wavelengths. It will be appreciated that the stack 660 may correspond to the stack 260 (FIG. 6) and the illustrated waveguides of the stack 660 may correspond to part of the plurality of waveguides 270, 280, 290, 300, 310, except that light from one or more of the image injection devices 360, 370, 380, 390, 400 is injected into the waveguides from a position that requires light to be redirected for in-coupling.

The illustrated set 660 of stacked waveguides includes waveguides 670, 680, and 690. Each waveguide includes an associated in-coupling optical element (which may also be referred to as a light input area on the waveguide), with, e.g., in-coupling optical element 700 disposed on a major surface (e.g., an upper major surface) of waveguide 670, in-coupling optical element 710 disposed on a major surface (e.g., an upper major surface) of waveguide 680, and in-coupling optical element 720 disposed on a major surface (e.g., an upper major surface) of waveguide 690. In some embodiments, one or more of the in-coupling optical elements 700, 710, 720 may be disposed on the bottom major surface of the respective waveguide 670, 680, 690 (particularly where the one or more in-coupling optical elements are reflective, deflecting optical elements). As illustrated, the in-coupling optical elements 700, 710, 720 may be disposed on the upper major surface of their respective waveguide 670, 680, 690 (or the top of the next lower waveguide), particularly where those in-coupling optical elements are transmissive, deflecting optical elements. In some embodiments, the in-coupling optical elements 700, 710, 720 may be disposed in the body of the respective waveguide 670, 680, 690. In some embodiments, as discussed herein, the in-coupling optical elements 700, 710, 720 are wavelength selective, such that they selectively redirect one or more wavelengths of light, while transmitting other wavelengths of light. While illustrated on one side or corner of their respective waveguide 670, 680, 690, it will be appreciated that the in-coupling optical elements 700, 710, 720 may be disposed in other areas of their respective waveguide 670, 680, 690 in some embodiments.

As illustrated, the in-coupling optical elements 700, 710, 720 may be laterally offset from one another, as seen in the illustrated head-on view in a direction of light propagating to these in-coupling optical elements. In some embodiments, each in-coupling optical element may be offset such that it receives light without that light passing through another in-coupling optical element. For example, each in-coupling optical element 700, 710, 720 may be configured to receive light from a different image injection device 360, 370, 380, 390, and 400 as shown in FIG. 6, and may be separated (e.g., laterally spaced apart) from other in-coupling optical elements 700, 710, 720 such that it substantially does not receive light from the other ones of the in-coupling optical elements 700, 710, 720.

Each waveguide also includes associated light distributing elements, with, e.g., light distributing elements 730 disposed on a major surface (e.g., a top major surface) of waveguide 670, light distributing elements 740 disposed on a major surface (e.g., a top major surface) of waveguide 680, and light distributing elements 750 disposed on a major surface (e.g., a top major surface) of waveguide 690. In some other embodiments, the light distributing elements 730, 740, 750, may be disposed on a bottom major surface of associated waveguides 670, 680, 690, respectively. In some other embodiments, the light distributing elements 730, 740, 750, may be disposed on both top and bottom major surface of associated waveguides 670, 680, 690, respectively; or the light distributing elements 730, 740, 750, may be disposed on different ones of the top and bottom major surfaces in different associated waveguides 670, 680, 690, respectively.

The waveguides 670, 680, 690 may be spaced apart and separated by, e.g., gas, liquid, and/or solid layers of material. For example, as illustrated, layer 760a may separate waveguides 670 and 680; and layer 760b may separate waveguides 680 and 690. In some embodiments, the layers 760a and 760b are formed of low refractive index materials (that is, materials having a lower refractive index than the material forming the immediately adjacent one of waveguides 670, 680, 690). Preferably, the refractive index of the material forming the layers 760*a*, 760*b* is 0.05 or more, or 0.10 or less than the refractive index of the material forming the waveguides 670, 680, 690. Advantageously, the lower refractive index layers 760*a*, 760*b* may function as cladding layers that facilitate total internal reflection (TIR) of light through the waveguides 670, 680, 690 (e.g., TIR between the top and bottom major surfaces of each waveguide). In some embodiments, the layers 760*a*, 760*b* are formed of air. While not illustrated, it will be appreciated that the top and bottom of the illustrated set 660 of waveguides may include immediately neighboring cladding layers.

Preferably, for ease of manufacturing and other considerations, the material forming the waveguides 670, 680, 690 are similar or the same, and the material forming the layers 760*a*, 760*b* are similar or the same. In some embodiments, the material forming the waveguides 670, 680, 690 may be different between one or more waveguides, and/or the material forming the layers 760*a*, 760*b* may be different, while still holding to the various refractive index relationships noted above.

With continued reference to FIG. 9A, light rays 770, 780, 790 are incident on the set 660 of waveguides. It will be appreciated that the light rays 770, 780, 790 may be injected into the waveguides 670, 680, 690 by one or more image injection devices 360, 370, 380, 390, 400 (FIG. 6).

In some embodiments, the light rays 770, 780, 790 have different properties, e.g., different wavelengths or different ranges of wavelengths, which may correspond to different colors. The in-coupling optical elements 700, 710, 720 each deflect the incident light such that the light propagates through a respective one of the waveguides 670, 680, 690 by TIR. In some embodiments, the in-coupling optical elements 700, 710, 720 each selectively deflect one or more particular wavelengths of light, while transmitting other wavelengths to an underlying waveguide and associated in-coupling optical element.

For example, in-coupling optical element 700 may be configured to deflect ray 770, which has a first wavelength or range of wavelengths, while transmitting rays 780 and 790, which have different second and third wavelengths or ranges of wavelengths, respectively. The transmitted ray 780 impinges on and is deflected by the in-coupling optical element 710, which is configured to deflect light of a second wavelength or range of wavelengths. The ray 790 is deflected by the in-coupling optical element 720, which is configured to selectively deflect light of third wavelength or range of wavelengths.

With continued reference to FIG. 9A, the deflected light rays 770, 780, 790 are deflected so that they propagate through a corresponding waveguide 670, 680, 690; that is, the in-coupling optical elements 700, 710, 720 of each waveguide deflects light into that corresponding waveguide 670, 680, 690 to in-couple light into that corresponding waveguide. The light rays 770, 780, 790 are deflected at angles that cause the light to propagate through the respective waveguide 670, 680, 690 by TIR. The light rays 770, 780, 790 propagate through the respective waveguide 670, 680, 690 by TIR until impinging on the waveguide's corresponding light distributing elements 730, 740, 750.

Figure 9B:
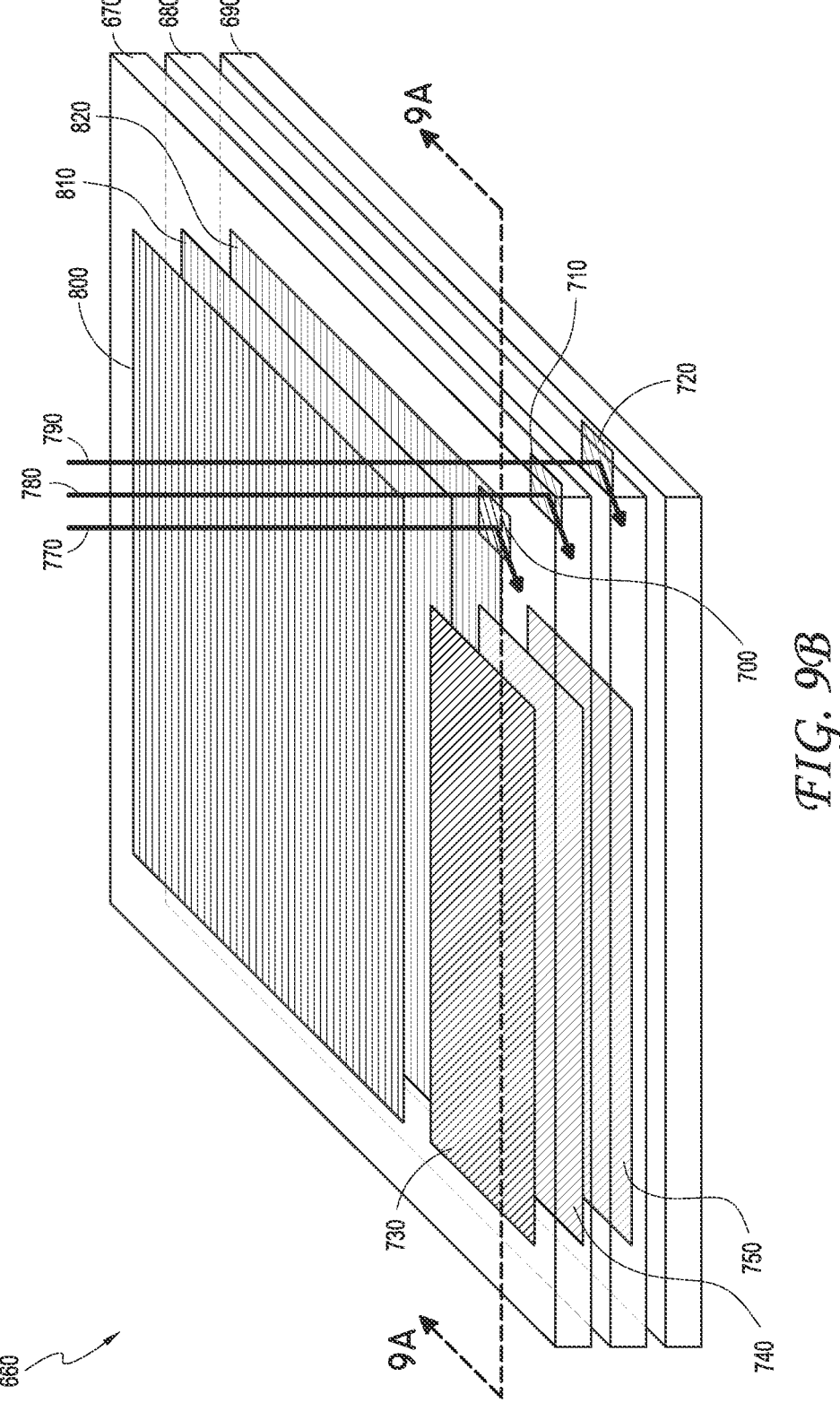
FIG. 9B illustrates a perspective view of an example of the plurality of stacked waveguides of FIG. 9A.

With reference now to FIG. 9B, a perspective view of an example of the plurality of stacked waveguides of FIG. 9A is illustrated. As noted above, the in-coupled light rays 770, 780, 790, are deflected by the in-coupling optical elements 700, 710, 720, respectively, and then propagate by TIR within the waveguides 670, 680, 690, respectively. The light rays 770, 780, 790 then impinge on the light distributing elements 730, 740, 750, respectively. The light distributing elements 730, 740, 750 deflect the light rays 770, 780, 790 so that they propagate towards the out-coupling optical elements 800, 810, 820, respectively.

In some embodiments, the light distributing elements 730, 740, 750 are orthogonal pupil expanders (OPE's). In some embodiments, the OPE's deflect or distribute light to the out-coupling optical elements 800, 810, 820 and, in some embodiments, may also increase the beam or spot size of this light as it propagates to the out-coupling optical elements. In some embodiments, the light distributing elements 730, 740, 750 may be omitted and the in-coupling optical elements 700, 710, 720 may be configured to deflect light directly to the out-coupling optical elements 800, 810, 820. For example, with reference to FIG. 9A, the light distributing elements 730, 740, 750 may be replaced with out-coupling optical elements 800, 810, 820, respectively. In some embodiments, the out-coupling optical elements 800, 810, 820 are exit pupils (EP's) or exit pupil expanders (EPE's) that direct light in a viewer's eye 210 (FIG. 7). It will be appreciated that the OPE's may be configured to increase the dimensions of the eye box in at least one axis and the EPE's may be to increase the eye box in an axis crossing, e.g., orthogonal to, the axis of the OPEs. For example, each OPE may be configured to redirect a portion of the light striking the OPE to an EPE of the same waveguide, while allowing the remaining portion of the light to continue to propagate down the waveguide. Upon impinging on the OPE again, another portion of the remaining light is redirected to the EPE, and the remaining portion of that portion continues to propagate further down the waveguide, and so on. Similarly, upon striking the EPE, a portion of the impinging light is directed out of the waveguide towards the user, and a remaining portion of that light continues to propagate through the waveguide until it strikes the EP again, at which time another portion of the impinging light is directed out of the waveguide, and so on. Consequently, a single beam of in-coupled light may be "replicated" each time a portion of that light is redirected by an OPE or EPE, thereby forming a field of cloned beams of light, as shown in FIG. 6. In some embodiments, the OPE and/or EPE may be configured to modify a size of the beams of light.

Accordingly, with reference to FIGS. 9A and 9B, in some embodiments, the set 660 of waveguides includes waveguides 670, 680, 690; in-coupling optical elements 700, 710, 720; light distributing elements (e.g., OPE's) 730, 740, 750; and out-coupling optical elements (e.g., EP's) 800, 810, 820 for each component color. The waveguides 670, 680, 690 may be stacked with an air gap/cladding layer between each one. The in-coupling optical elements 700, 710, 720 redirect or deflect incident light (with different in-coupling optical elements receiving light of different wavelengths) into its waveguide. The light then propagates at an angle which will result in TIR within the respective waveguide 670, 680, 690. In the example shown, light ray 770 (e.g., blue light) is deflected by the first in-coupling optical element 700, and then continues to bounce down the waveguide, interacting with the light distributing element (e.g., OPE's) 730 and then the out-coupling optical element (e.g., EPs) 800, in a manner described earlier. The light rays 780 and 790 (e.g., green and red light, respectively) will pass through the waveguide 670, with light ray 780 impinging on and being deflected by in-coupling optical element 710. The light ray 780 then bounces down the waveguide 680 via TIR, proceeding on to its light distributing element (e.g., OPEs) 740 and then the out-coupling optical element (e.g., EP's) 810. Finally, light ray 790 (e.g., red light) passes through the waveguide 690 to impinge on the light in-coupling optical elements 720 of the waveguide 690. The light in-coupling optical elements 720 deflect the light ray 790 such that the light ray propagates to light distributing element (e.g., OPEs) 750 by TIR, and then to the out-coupling optical element (e.g., EPs) 820 by TIR. The out-coupling optical element 820 then finally out-couples the light ray 790 to the viewer, who also receives the out-coupled light from the other waveguides 670, 680.

Figure 9C:
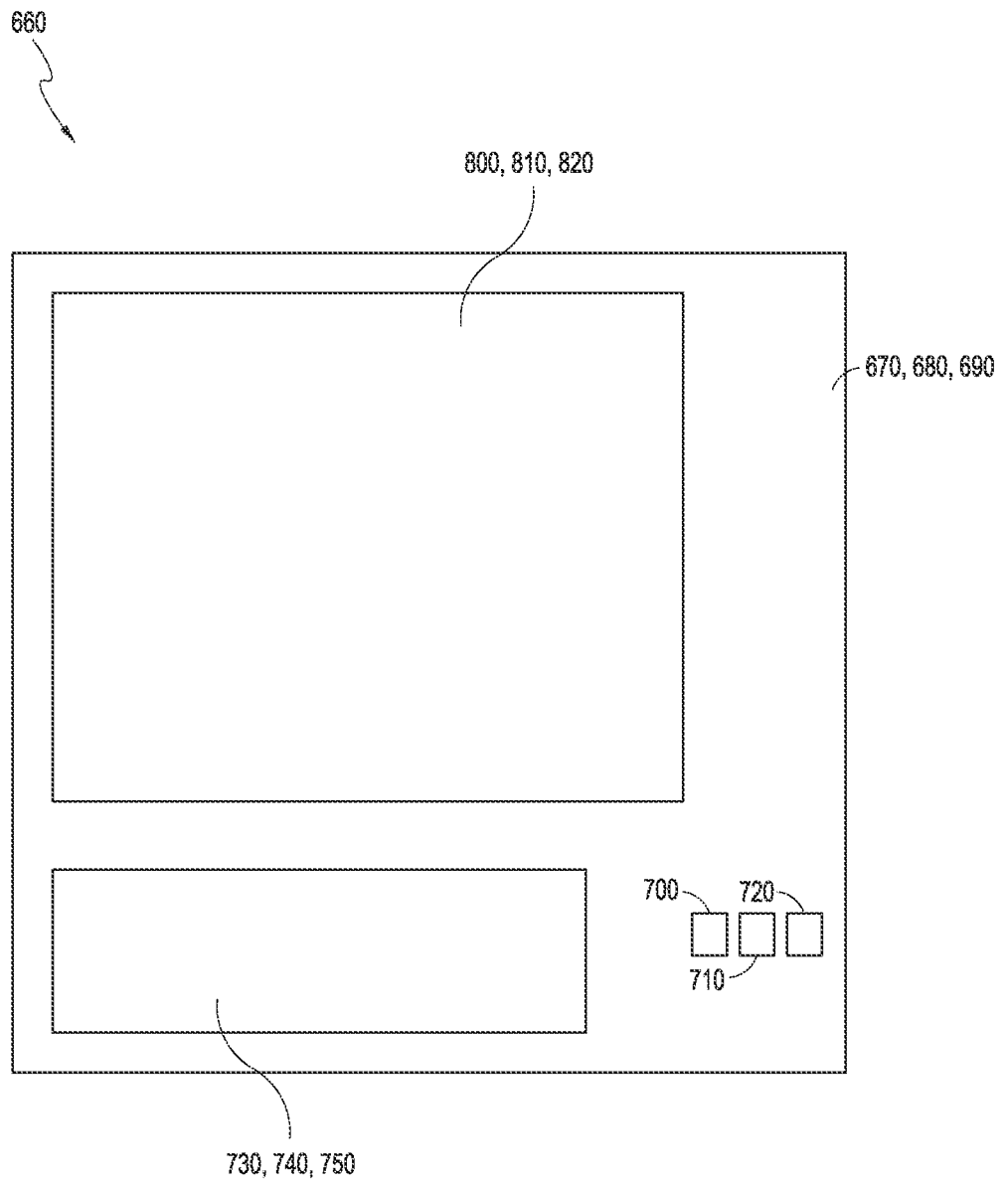
FIG. 9C illustrates a top-down plan view of an example of the plurality of stacked waveguides of FIGS. 9A and 9B.

FIG. 9C illustrates a top-down plan view of an example of the plurality of stacked waveguides of FIGS. 9A and 9B. It will be appreciated that this top-down view may also be referred to as a head-on view, as seen in the direction of propagation of light towards the in-coupling optical elements 800, 810, 820; that is, the top-down view is a view of the waveguides with image light incident normal to the page. As illustrated, the waveguides 670, 680, 690, along with each waveguide's associated light distributing element 730, 740, 750 and associated out-coupling optical element 800, 810, 820, may be vertically aligned. However, as discussed herein, the in-coupling optical elements 700, 710, 720 are not vertically aligned; rather, the in-coupling optical elements are preferably non-overlapping (e.g., laterally spaced apart as seen in the top-down view). As discussed further herein, this nonoverlapping spatial arrangement facilitates the injection of light from different sources into different waveguides on a one-to-one basis, thereby allowing a specific light source to be uniquely coupled to a specific waveguide. In some embodiments, arrangements including nonoverlapping spatially-separated in-coupling optical elements may be referred to as a shifted pupil system, and the in-coupling optical elements within these arrangements may correspond to sub-pupils.

It will be appreciated that the spatially overlapping areas may have lateral overlap of 70% or more, 80% or more, or 90% or more of their areas, as seen in the top-down view. On the other hand, the laterally shifted areas of less than 30% overlap, less than 20% overlap, or less than 10% overlap of their areas, as seen in top-down view. In some embodiments, laterally shifted areas have no overlap.

Figure 9D:
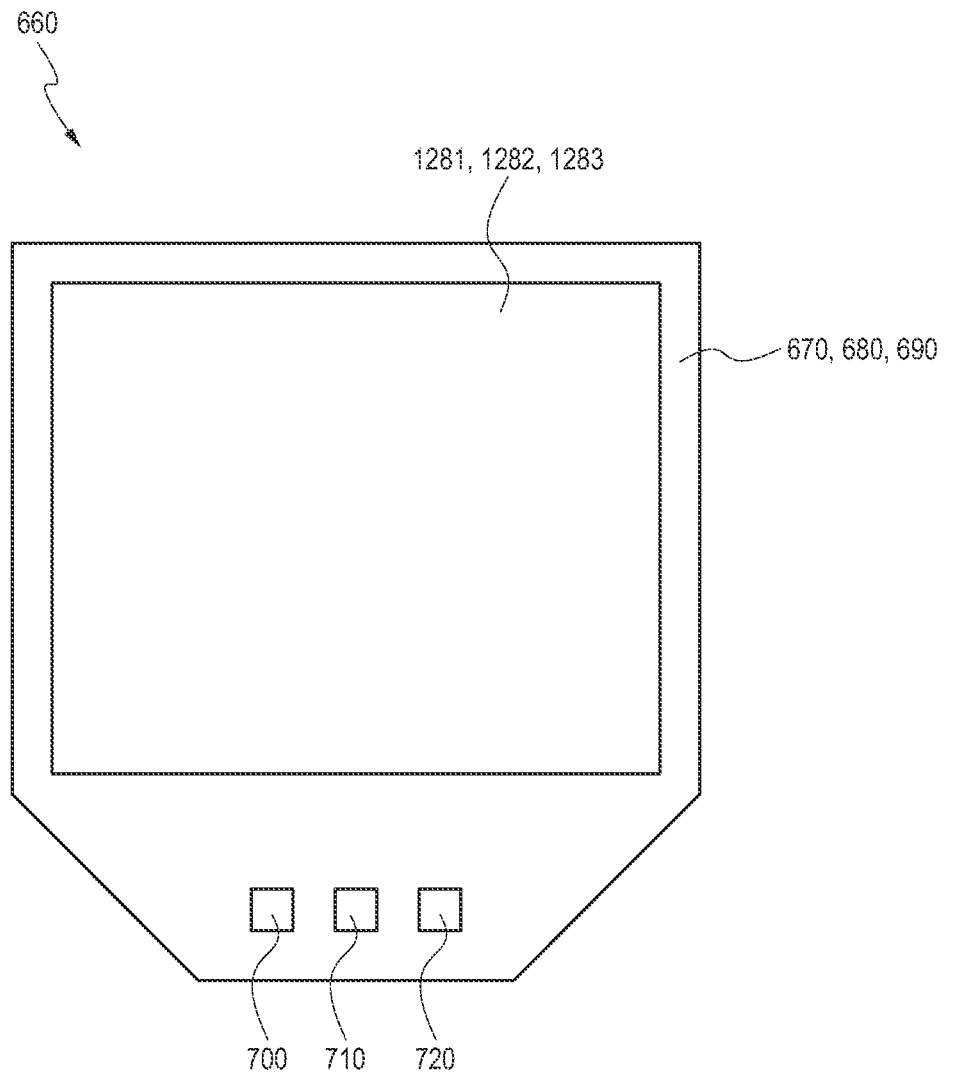
FIG. 9D illustrates a top-down plan view of another example of a plurality of stacked waveguides.

FIG. 9D illustrates a top-down plan view of another example of a plurality of stacked waveguides. As illustrated, the waveguides 670, 680, 690 may be vertically aligned. However, in comparison to the configuration of FIG. 9C, separate light distributing elements 730, 740, 750 and associated out-coupling optical elements 800, 810, 820 are omitted. Instead, light distributing elements and out-coupling optical elements are effectively superimposed and occupy the same area as seen in the top-down view. In some embodiments, light distributing elements (e.g., OPE's) may be disposed on one major surface of the waveguides 670, 680, 690 and out-coupling optical elements (e.g., EPE's) may be disposed on the other major surface of those waveguides. Thus, each waveguide 670, 680, 690 may have superimposed light distributing and out coupling optical elements, collectively referred to as combined OPE/EPE's 1281, 1282, 1283, respectively. Further details regarding such combined OPE/EPE's may be found in U.S. application Ser. No. 16/221,359, filed on Dec. 14, 2018, the entire disclosure of which is incorporated by reference herein. The in-coupling optical elements 700, 710, 720 in-couple and direct light to the combined OPE/EPE's 1281, 1282, 1283, respectively. In some embodiments, as illustrated, the in-coupling optical elements 700, 710, 720 may be laterally shifted (e.g., they are laterally spaced apart as seen in the illustrated top-down view) in have a shifted pupil spatial arrangement. As with the configuration of FIG. 9C, this laterally-shifted spatial arrangement facilitates the injection of light of different wavelengths (e.g., from different light sources) into different waveguides on a one-to-one basis.

Figure 9E:
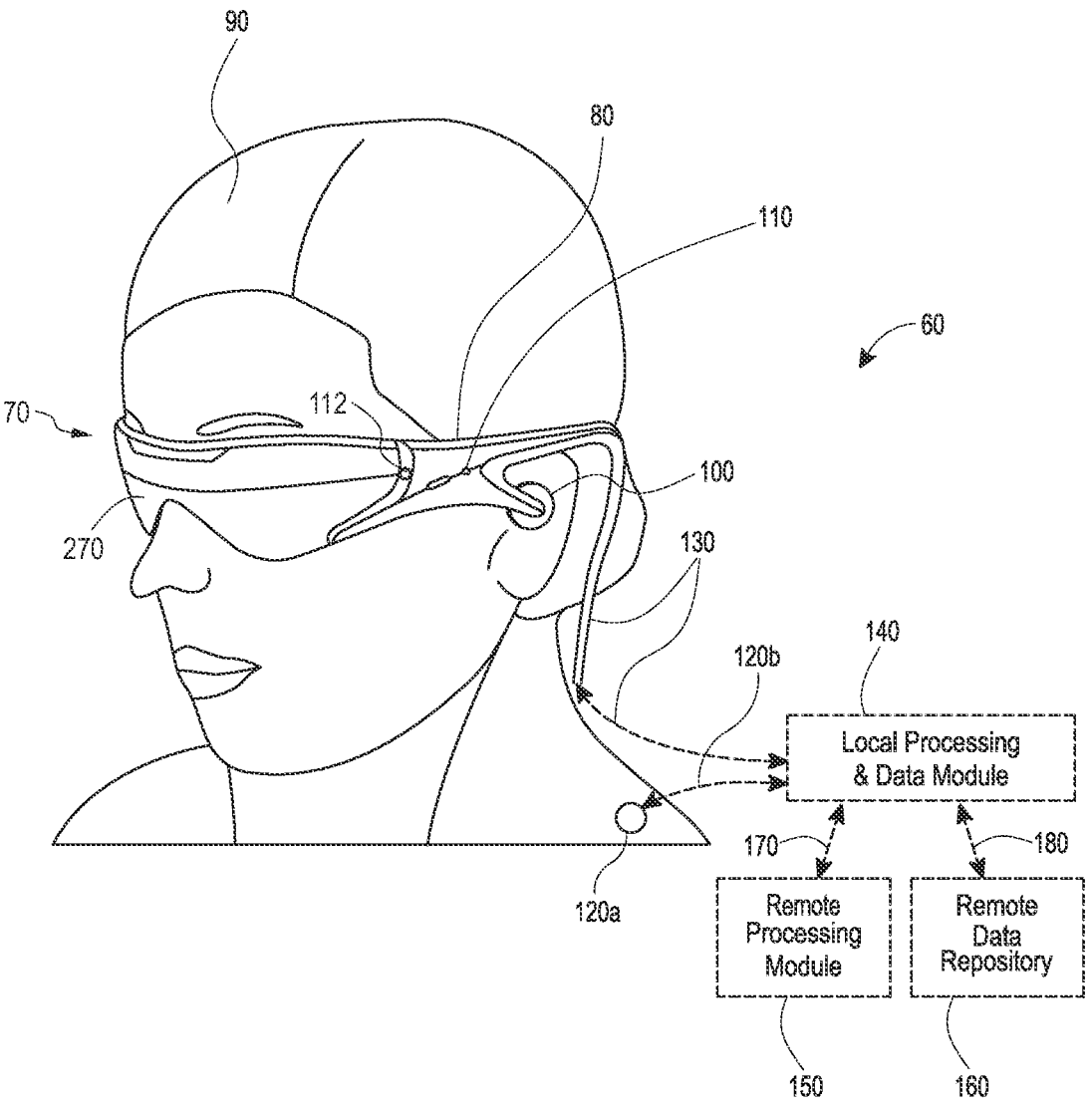
FIG. 9E illustrates an example of wearable display system.

FIG. 9E illustrates an example of wearable display system 60 into which the various waveguides and related systems disclosed herein may be integrated. In some embodiments, the display system 60 is the system 250 of FIG. 6, with FIG. 6 schematically showing some parts of that system 60 in greater detail. For example, the waveguide assembly 260 of FIG. 6 may be part of the display 70.

With continued reference to FIG. 9E, the display system 60 includes a display 70, and various mechanical and electronic modules and systems to support the functioning of that display 70. The display 70 may be coupled to a frame 80, which is wearable by a display system user or viewer 90 and which is configured to position the display 70 in front of the eyes of the user 90. The display 70 may be considered eyewear in some embodiments. The display 70 may include one or more waveguides, such as the waveguide 270, configured to relay in-coupled image light and to output that image light to an eye of the user 90. In some embodiments, a speaker 100 is coupled to the frame 80 and configured to be positioned adjacent the ear canal of the user 90 (in some embodiments, another speaker, not shown, may optionally be positioned adjacent the other ear canal of the user to provide stereo/shapeable sound control). The display system 60 may also include one or more microphones 110 or other devices to detect sound. In some embodiments, the microphone is configured to allow the user to provide inputs or commands to the system 60 (e.g., the selection of voice menu commands, natural language questions, etc.), and/or may allow audio communication with other persons (e.g., with other users of similar display systems. The microphone may further be configured as a peripheral sensor to collect audio data (e.g., sounds from the user and/or environment). In some embodiments, the display system 60 may further include one or more outwardly-directed environmental sensors 112 configured to detect objects, stimuli, people, animals, locations, or other aspects of the world around the user. For example, environmental sensors 112 may include one or more cameras, which may be located, for example, facing outward so as to capture images similar to at least a portion of an ordinary field of view of the user 90. In some embodiments, the display system may also include a peripheral sensor 120a, which may be separate from the frame 80 and attached to the body of the user 90 (e.g., on the head, torso, an extremity, etc. of the user 90). The peripheral sensor 120a may be configured to acquire data characterizing a physiological state of the user 90 in some embodiments. For example, the sensor 120a may be an electrode.

With continued reference to FIG. 9E, the display 70 is operatively coupled by communications link 130, such as by a wired lead or wireless connectivity, to a local data processing module 140 which may be mounted in a variety of configurations, such as fixedly attached to the frame 80, fixedly attached to a helmet or hat worn by the user, embedded in headphones, or otherwise removably attached to the user 90 (e.g., in a backpack-style configuration, in a belt-coupling style configuration). Similarly, the sensor 120a may be operatively coupled by communications link 120b, e.g., a wired lead or wireless connectivity, to the local processor and data module 140. The local processing and data module 140 may comprise a hardware processor, as well as digital memory, such as non-volatile memory (e.g., flash memory or hard disk drives), both of which may be utilized to assist in the processing, caching, and storage of data. Optionally, the local processor and data module 140 may include one or more central processing units (CPUs), graphics processing units (GPUs), dedicated processing hardware, and so on. The data may include data a) captured from sensors (which may be, e.g., operatively coupled to the frame 80 or otherwise attached to the user 90), such as image capture devices (such as cameras), microphones, inertial measurement units, accelerometers, compasses, GPS units, radio devices, gyros, and/or other sensors disclosed herein; and/or b) acquired and/or processed using remote processing module 150 and/or remote data repository 160 (including data relating to virtual content), possibly for passage to the display 70 after such processing or retrieval. The local processing and data module 140 may be operatively coupled by communication links 170, 180, such as via a wired or wireless communication links, to the remote processing module 150 and remote data repository 160 such that these remote modules 150, 160 are operatively coupled to each other and available as resources to the local processing and data module 140. In some embodiments, the local processing and data module 140 may include one or more of the image capture devices, microphones, inertial measurement units, accelerometers, compasses, GPS units, radio devices, and/or gyros. In some other embodiments, one or more of these sensors may be attached to the frame 80, or may be standalone structures that communicate with the local processing and data module 140 by wired or wireless communication pathways.

With continued reference to FIG. 9E, in some embodiments, the remote processing module 150 may comprise one or more processors configured to analyze and process data and/or image information, for instance including one or more central processing units (CPUs), graphics processing units (GPUs), dedicated processing hardware, and so on. In some embodiments, the remote data repository 160 may comprise a digital data storage facility, which may be available through the internet or other networking configuration in a "cloud" resource configuration. In some embodiments, the remote data repository 160 may include one or more remote servers, which provide information, e.g., information for generating virtual content, to the local processing and data module 140 and/or the remote processing module 150. In some embodiments, all data is stored and all computations are performed in the local processing and data module, allowing fully autonomous use from a remote module. Optionally, an outside system (e.g., a system of one or more processors, one or more computers) that includes CPUs, GPUs, and so on, may perform at least a portion of processing (e.g., generating image information, processing data) and provide information to, and receive information from, modules 140, 150, 160, for instance via wireless or wired connections.

Sensitivity Measures

As described above, a display device (e.g., display device 60) may be used to provide health information regarding users. Certain display devices, such as display devices with different configurations and/or implementing different oculometric protocols, may be more sensitive to certain physiological conditions and/or cohorts of persons. As will be described, a sensitivity measure may be determined which represents a distance measure between a control population and an experimental population. The sensitivity measure may be determined for a particular configuration of display device and/or a particular oculometric protocol. Different sensitivity measures may be compared (e.g., an "A/B" comparison), allowing different configurations and/or oculometric protocols to be easily compared. In this way, certain configurations and/or oculometric protocols may be determined to be advantageous (e.g., most sensitive) to experimental populations.

To determine the sensitivity measure, eye-tracking information may be obtained and analyzed by a system. The eye-tracking information may include eye-tracking metrics for the control population and experimental population. These eye-tracking metrics may represent different metrics obtained while persons in the control and experimental populations were using a same configuration of display device and/or viewing a same oculometric protocol. Based on the eye-tracking metrics, the system may then determine the sensitivity measure described herein.

Example description related to tracking of a user's eyes is included in U.S. Patent Pub. No. 2019/0243448, the entirety of which is incorporated herein by reference. Further example description related to tracking of a user's, and determining health and/or condition information, is included in U.S. Patent Pub. 2016/0270656.

Figure 10:
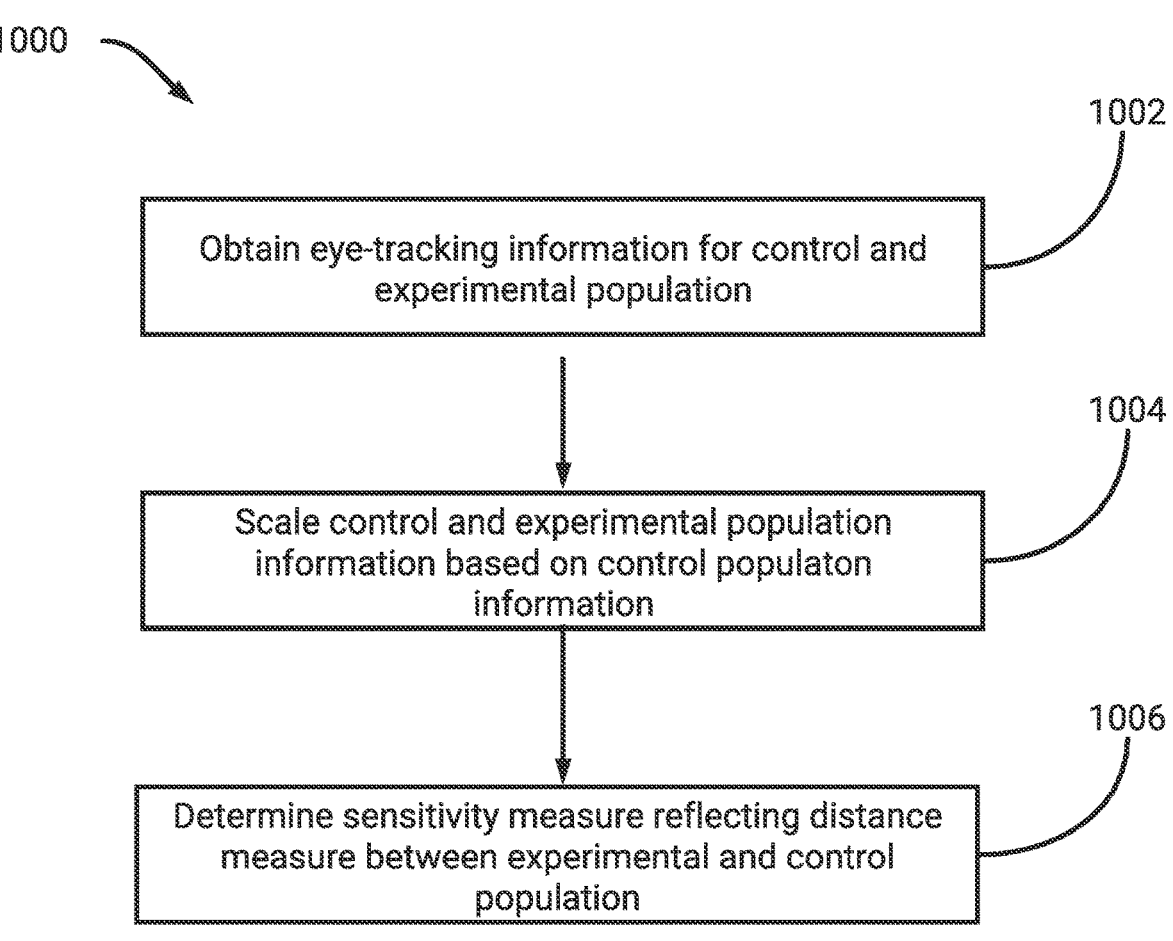
FIG. 10 is a flowchart for an example process for determining a sensitivity measure.

FIG. 10 is a flowchart for an example process 1000 for determining a sensitivity measure. For convenience, the process 1000 will be described as being performed by a system of one or more computers. An example system may optionally provide information to example display devices used by users. For example, the system may request eye-tracking information from display devices associated with a same configuration. As another example, the system may request eye-tracking information from display devices, such as devices using a same oculometric protocol. In some embodiments, the system may instruct display devices to assume a particular configuration and/or use a particular oculometric protocol.

At block 1002, the system obtains eye-tracking information for a control population and an experimental population. The system may obtain eye-tracking information from display devices used by users included in the control population and the experimental population. These display devices may have a same configuration, such as same image sensors, same placement of the image sensors, same techniques to track eyes, and so on. Additionally, these display devices may implement a same oculometric protocol. For example, an oculometric protocol may define particular virtual content to present to a user. The experimental population may optionally include users who have one or more same physiological conditions and/or are included in a same cohort.

The eye-tracking information may reflect eye-tracking metrics for each user included in the control population and experimental population. These metrics may be determined, for example, by a display device used by each user. In some embodiments, the system may receive raw eye-tracking information and may determine the eye-tracking metrics. For example, the raw eye-tracking information may indicate position information associated with a user's eyes. Example eye-tracking metrics may include latency information, eye acceleration information, saccade information, responsiveness information, path of movement of the eye, and so on. Some example eye-tracking metrics are described in more detail in "Oculometric Assessment of Sensorimotor Impairment Associated with TBI," which is incorporated by reference and forms part of the disclosure as if set forth herein.

For ease of reference, there may be "M" eye-tracking metrics along with N users included in the control population. The system may, in some embodiments, organize this information into a matrix of N rows and M columns. Additionally, there may be Q users included in the experimental population.

At block 1004, the system scales the control and experimental population information based on the control population information. In some embodiments, the system determines a median and standard deviation of the eye-tracking metrics across the control population. Thus, the system may compute a [1×M] vector comprising measures of central tendency (e.g., median, mean, mode) of the eye-tracking metrics. Additionally, the system may determine a covariance matrix based on the control population's eye-tracking metrics. This covariance matrix may thus be an [M×M] matrix.

The system may then scale the control population information based on the median and standard deviation. For example, for each of the M control population users, the system may subtract the median and scale by the standard deviation for a corresponding eye-tracking metric.

In some embodiments, the system may scale the experimental population information based on the median and standard deviation. For example, for each of the Q experimental population users, the system may subtract the median and scale by the standard deviation for a corresponding eye-tracking metric.

At block 1006, the system determines a sensitivity measure. As described above, the system may determine a value (e.g., a scalar value) representing a distance measure between the control and experimental populations. In this way, the sensitivity measure may reflect a sensitivity of the display device discriminating between users in the control population and users in the experimental population based on the eye-tracking information.

In some embodiments, the system determines a scalar index for each user in the control population and experimental population. The scalar index may represent a likelihood metric and may be computed as a dot product between a user's scaled eye-tracking metrics and a predefined template. The template may represent a template for deficits or improvements, as known in the art. This dot product may then be scaled to account for clustering in the covariance matrix of the control population. In this way, a unit normal distribution (e.g., zero mean, unit variance) for the control population may be achieved.

These scalar indexes may then be included a [1×N] vector for the control population and a [1×1Q] vector for the experimental population.

The system determines the sensitivity measure based on these scalar indexes. For example, the system may compute a d' distance measure based on the control population being unit normal. For example, the system may compute:

$$d' = \frac{\text{median } [1 \times Q] \text{ scalar index vector}}{\left(.5 * \left(std([1 \times Q] \text{ index vector})^2 + 1\right)\right)^{\frac{1}{2}}}$$

where "std" represents a standard deviation operation.

An example table with example sensitivity measures d' is reproduced below with respect to Table 1.

TABLE 1

Oculometric sensitivity for several experimental populations.

| Population[a] | n | μ | σ | d' | ROC | Control[b] | n | Citation |
|---|---|---|---|---|---|---|---|---|
| HE, decompensated | 19 | −2.1 | 1.2 | −1.9 | 0.88 | [31] | 19 | [31] |

TABLE 1-continued

Oculometric sensitivity for several experimental populations.

| Population[a] | n | μ | σ | d' | ROC | Control[b] | n | Citation |
|---|---|---|---|---|---|---|---|---|
| Chronic TBI, civilian | 34 | −1.6 | 1.4 | −1.3 | 0.83 | [19] | 41 | [28] |
| Chronic TBI, veteran | 8 | −1.5 | 1.2 | −1.3 | 0.77 | [19] | 41 | [32] |
| HE, compensated | 10 | −1.1 | 1.2 | −1.0 | 0.71 | [31] | 19 | [31] |
| Parkinson's Disease | 45 | −1.0 | 1.2 | −0.9 | 0.72 | [33] | 25 | [33] |
| Baseball, 2018 MiLB | 38 | −0.1 | 1.2 | −0.1 | 0.57 | [19] | 41 | Current |
| Baseball, HK National | 44 | 0.8 | 0.7 | 0.9 | 0.76 | [27] | 47 | [27] |

In some embodiments, the further the sensitivity value (e.g., d') is from 0, the more sensitivity the particular configuration and/or oculometric protocol is for the physiological condition and/or cohort. For example, Table 1 may be associated with a particular configuration of a display device. Table 1 reflects different experimental populations and associated information. In this example, the particular configuration may be more sensitive to an experimental population which includes users who have hepatic encephalopathy (HE) decompensated as compared to users who have HE compensated.

Figure 11:
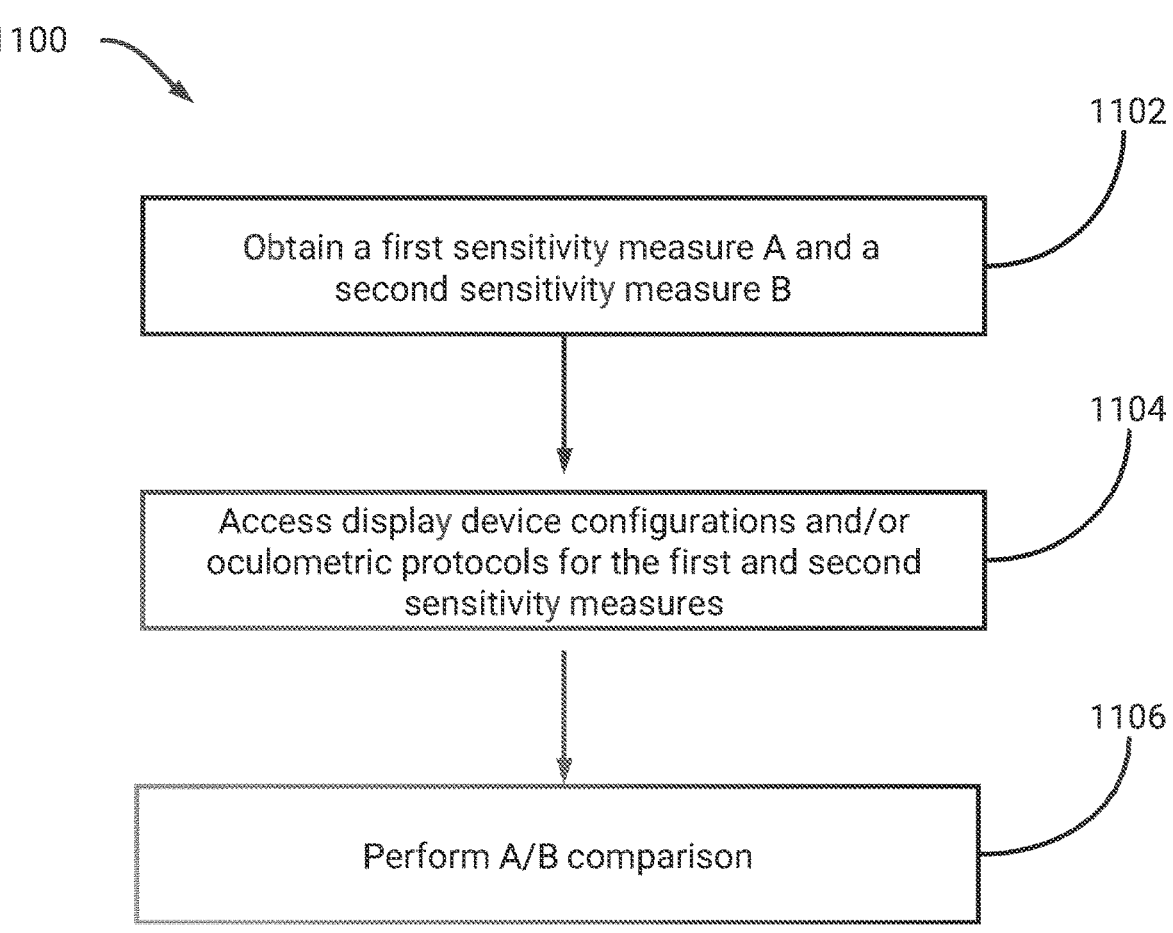
FIG. 11 is a flowchart for an example process for comparing sensitivity measures.

FIG. 11 is a flowchart for an example process 1000 for determining a sensitivity measure. For convenience, the process 1100 will be described as being performed by a system of one or more computers (e.g., the system described in FIG. 10).

At block 1102, the system obtains a first sensitivity measure and a second sensitivity measure. The first sensitivity measure and second sensitivity measure may have been generated for a same, or substantially similar, experimental population and a same, or substantially similar, control population. For example, the experimental population may fall within a same cohort and/or include users with a same physiological condition.

At block 1104, the systems accesses information identifying display device configurations and/or oculometric protocols for the first and second sensitivity measures. For example, the first sensitivity measure may have been generated based on eye-tracking information from display devices with a different configuration as compared to the second sensitivity measure. An example different configuration may include a different frequency at which eye movements are tracked. As another example, the first sensitivity measure may have been generated based on eye-tracking information from display devices implementing a different oculometric protocol. An example different oculometric protocol may include presenting different visual stimuli, presenting stimuli at different perceived depths or depth planes, and so on. Thus, the first and second sensitivity measures may have been generated based on presenting stimuli at different depth planes (e.g., on different depth planes).

At block 1106, the system performs A/B comparisons. The system may compare the first sensitivity measure and second sensitivity measure, such as by determining a ratio between them. The system may thus determine which of the sensitivity measures is more sensitive to the experimental population. In some embodiments, the system may compare a multitude of sensitivity measures for the experimental population. Based on these comparisons, the system may determine certain features which are indicative, or otherwise appear to correlate with, higher sensitivity. For example, the system may determine that certain placements of image sensors are associated with higher sensitivity for the experimental population.

In general, the system may evaluate the ability to screen for diseases using tasks designed to assess different cognitive domains: attention, impulse control, sensorimotor performance, memory, binding of object features, or physiological signs (e.g., tremor). For example, a memory task may be more effective than a smooth pursuit task to detect early signs of Alzheimer's disease, with disease processes that form in the hippocampus and spread outward, and so on.

Based on the sensitivity measures, the system may determine a particular configuration and/or particular oculometric protocol which is most sensitive to an experimental population. A user of a display device may, in some embodiments, undergo testing to determine whether the user falls within a particular experimental population. For example, the display device may perform testing when the user first puts on the display device and/or when the user selects an option to perform the testing.

As an example, the display device may adjust certain features of its configuration. For example, the display device may rotate, move, and so on, its image sensors to obtain image of the user's eye, or may provide instructions (e.g., to a user) to make adjustments to increase sensitivity. The display device may also adjust illumination (e.g., an amount of light, illumination frequencies, and so on). The display device may also adjust techniques to track the user's eyes. These adjustments may cause the display device to assume different configurations which are most sensitive to certain experimental populations. For each configuration, the display device may determine whether the user falls within an associated experimental population. As an example, the display device may generate eye-tracking metrics for the user. The display device may then determine measures of similarity between the eye-tracking metrics and eye-tracking for users in the associated experimental population. The display device may also perform the process 1000 described above using the user's eye-tracking metrics as the experimental population. Based on the resulting sensitivity measure the system may determine whether the user falls within the associated experimental population.

Similarly, the display device may adjust an oculometric protocol. For example, the display device may output different virtual content as described herein. In some embodiments, the display device may adjust its configuration and also adjust the oculometric protocol.

Other Embodiments

Various example embodiments of the invention are described herein. Reference is made to these examples in a non-limiting sense. They are provided to illustrate more broadly applicable aspects of the invention. Various changes may be made to the invention described and equivalents may be substituted without departing from the spirit and scope of the invention.

For example, while advantageously utilized with AR displays that provide images across multiple depth planes, the virtual content disclosed herein may also be displayed by systems that provide images on a single depth plane.

In addition, many modifications may be made to adapt a particular situation, material, composition of matter, process, process act, or step(s) to the objective(s), spirit, or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

The invention includes methods that may be performed using the subject devices. The methods may comprise the act of providing such a suitable device. Such provision may be performed by the user. In other words, the "providing" act merely requires the user obtain, access, approach, position, set-up, activate, power-up or otherwise act to provide the requisite device in the subject method. Methods recited herein may be carried out in any order of the recited events that is logically possible, as well as in the recited order of events.

In addition, it will be appreciated that each of the processes, methods, and algorithms described herein and/or depicted in the figures may be embodied in, and fully or partially automated by, code modules executed by one or more physical computing systems, hardware computer processors, application-specific circuitry, and/or electronic hardware configured to execute specific and particular computer instructions. For example, computing systems may include general purpose computers (e.g., servers) programmed with specific computer instructions or special purpose computers, special purpose circuitry, and so forth. A code module may be compiled and linked into an executable program, installed in a dynamic link library, or may be written in an interpreted programming language. In some embodiments, particular operations and methods may be performed by circuitry that is specific to a given function.

Further, certain embodiments of the functionality of the present disclosure are sufficiently mathematically, computationally, or technically complex that application-specific hardware or one or more physical computing devices (utilizing appropriate specialized executable instructions) may be necessary to perform the functionality, for example, due to the volume or complexity of the calculations involved or to provide results substantially in real-time. For example, a video may include many frames, with each frame having millions of pixels, and specifically programmed computer hardware is necessary to process the video data to provide a desired image processing task or application in a commercially reasonable amount of time.

Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. In some embodiments, the non-transitory computer-readable medium may be part of one or more of the local processing and data module (140), the remote processing module (150), and remote data repository (160). The methods and modules (or data) may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed processes or process steps may be stored, persistently or otherwise, in any type of non-transitory, tangible computer storage or may be communicated via a computer-readable transmission medium.

Any processes, blocks, states, steps, or functionalities described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities may be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto may be performed in other sequences that are appropriate, for example, in serial, in parallel, or in some other manner. Tasks or events may be added to or removed from the disclosed example embodiments. Moreover, the separation of various system components in the embodiments described herein is for illustrative purposes and should not be understood as requiring such separation in all embodiments. It should be understood that the described program components, methods, and systems may generally be integrated together in a single computer product or packaged into multiple computer products.

Example aspects of the invention, together with details regarding material selection and manufacture have been set forth above. As for other details of the present invention, these may be appreciated in connection with the above-referenced patents and publications as well as generally known or appreciated by those with skill in the art. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims.

Accordingly, the claims are not intended to be limited to the embodiments shown herein, but are to be accorded the widest scope consistent with this disclosure, the principles and the novel features disclosed herein.

What is claimed is:

1. A computer-implemented system, comprising:
one or more computers; and
one or more computer memory devices interoperably coupled with the one or more computers and having tangible, non-transitory, machine-readable media storing one or more instructions that, when executed by the one or more computers, perform one or more operations, comprising:
obtaining a first sensitivity measure and a second sensitivity measure, wherein the first sensitivity measure and the second sensitivity measure are generated for a same experimental population and a similar control population;
accessing information identifying display device configurations or oculometric protocols for the first sensitivity measure and the second sensitivity measure;
performing a ratio comparison of the first sensitivity measure and the second sensitivity measure; and
determining which of the first sensitivity measure and the second sensitivity measure is more sensitive to the same experimental population.

2. The computer-implemented system of claim 1, wherein the same experimental population or the same control population falls within a same cohort or includes users with a same physiological condition.

3. The computer-implemented system of claim 1, wherein the first sensitivity measure is generated based on: 1) eye-tracking information from display devices with a different configuration compared to the second sensitivity measure or 2) eye-tracking information from display devices implementing a different oculometric protocol.

4. The computer-implemented system of claim 3, wherein the different configuration includes a different frequency at which eye movements are tracked.

5. The computer-implemented system of claim 3, wherein the different oculometric protocol includes different visual stimuli at different perceived depths or depth planes.

6. The computer-implemented system of claim 1, wherein performing the ratio comparison of the first sensitivity measure and the second sensitivity measure compares a multitude of sensitivity measures for the same experimental population.

7. A computer-implemented method, comprising:
obtaining a first sensitivity measure and a second sensitivity measure, wherein the first sensitivity measure and the second sensitivity measure are generated for a same experimental population and a same control population;
accessing information identifying display device configurations or oculometric protocols for the first sensitivity measure and the second sensitivity measure;
performing a ratio comparison of the first sensitivity measure and the second sensitivity measure; and determining which of the first sensitivity measure and the second sensitivity measure is more sensitive to the same experimental population.

8. The computer-implemented method of claim 7, wherein the same experimental population or the same control population falls within a same cohort or includes users with a same physiological condition.

9. The computer-implemented method of claim 7, wherein the first sensitivity measure is generated based on: 1) eye-tracking information from display devices with a different configuration compared to the second sensitivity measure or 2) eye-tracking information from display devices implementing a different oculometric protocol.

10. The computer-implemented method of claim 9, wherein the different configuration includes a different frequency at which eye movements are tracked.

11. The computer-implemented method of claim 9, wherein the different oculometric protocol includes different visual stimuli at different perceived depths or depth planes.

12. The computer-implemented method of claim 7, wherein performing the ratio comparison of the first sensitivity measure and the second sensitivity measure compares a multitude of sensitivity measures for the same experimental population.

13. The computer-implemented method of claim 7, comprising:

determining, based on the first sensitivity measure and the second sensitivity measure, a particular configuration or oculometric protocol which is most sensitive to the same experimental population.

14. A non-transitory, computer-readable medium storing one or more instructions executable by a computer system to perform one or more operations, comprising:

obtaining a first sensitivity measure and a second sensitivity measure, wherein the first sensitivity measure and the second sensitivity measure are generated for a same experimental population and a same control population;

accessing information identifying display device configurations or oculometric protocols for the first sensitivity measure and the second sensitivity measure;

performing a ratio comparison of the first sensitivity measure and the second sensitivity measure; and determining which of the first sensitivity measure and the second sensitivity measure is more sensitive to the same experimental population.

15. The non-transitory, computer-readable medium of claim 14, wherein the same experimental population or the same control population falls within a same cohort or includes users with a same physiological condition.

16. The non-transitory, computer-readable medium of claim 14, wherein the first sensitivity measure is generated based on: 1) eye-tracking information from display devices with a different configuration compared to the second sensitivity measure or 2) eye-tracking information from display devices implementing a different oculometric protocol.

17. The non-transitory, computer-readable medium of claim 16, wherein the different configuration includes a different frequency at which eye movements are tracked.

18. The non-transitory, computer-readable medium of claim 16, wherein the different oculometric protocol includes different visual stimuli at different perceived depths or depth planes.

19. The non-transitory, computer-readable medium of claim 14, wherein performing the ratio comparison of the first sensitivity measure and the second sensitivity measure compares a multitude of sensitivity measures for the same experimental population.

20. The non-transitory, computer-readable medium of claim 14, comprising:

determining, based on the first sensitivity measure and the second sensitivity measure, a particular configuration or oculometric protocol which is most sensitive to the same experimental population.

* * * * *